United States Patent
Usagawa

(10) Patent No.: US 9,857,322 B2
(45) Date of Patent: Jan. 2, 2018

(54) SEMICONDUCTOR GAS SENSOR

(71) Applicant: HITACHI, LTD., Chiyoda-ku, Tokyo (JP)

(72) Inventor: Toshiyuki Usagawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 138 days.

(21) Appl. No.: 14/893,062

(22) PCT Filed: May 23, 2013

(86) PCT No.: PCT/JP2013/064374
§ 371 (c)(1),
(2) Date: Nov. 21, 2015

(87) PCT Pub. No.: WO2014/188563
PCT Pub. Date: Nov. 27, 2014

(65) Prior Publication Data
US 2016/0097731 A1    Apr. 7, 2016

(51) Int. Cl.
*G01N 27/12*     (2006.01)
*G01N 27/414*    (2006.01)
*G01N 33/00*     (2006.01)

(52) U.S. Cl.
CPC ......... *G01N 27/12* (2013.01); *G01N 27/4148* (2013.01); *G01N 33/005* (2013.01)

(58) Field of Classification Search
CPC ... G01N 27/12; G01N 27/4148; G01N 33/005
(Continued)

(56) References Cited

U.S. PATENT DOCUMENTS 4,411,741 A * 10/1983 Janata ............... G01N 27/4141
                                                204/406
6,521,109 B1  2/2003 Bartic et al.
(Continued)

FOREIGN PATENT DOCUMENTS

JP      6-249826 A    9/1994
JP    2001-147215 A   5/2001
(Continued)

OTHER PUBLICATIONS

English Machine Translation of Takahiro, JP H06-249826 A, Sep. 9, 1994, Translated May 2017.*
English Machine Translation of Usagawa et al, JP 2009-300297 A, Dec. 24, 2009, Translated May 2017.*
Lundström, I. et al.; "A hydrogen-sensitive MOS field-effect transistor"; Applied Physics Letters; vol. 26; No. 2; pp. 55-57; (1975).
(Continued)

*Primary Examiner* — Hezron E Williams
*Assistant Examiner* — David Z Huang
(74) *Attorney, Agent, or Firm* — Miles & Stockbridge P.C.

(57) ABSTRACT

A semiconductor gas sensor includes a CMOS inverter which is configured by an n-channel field effect transistor having a catalytic gate and a p-channel field effect transistor having the catalytic gate. An input setting gate potential Vin(D) of the CMOS inverter is set to satisfy "Vin(D)=Vtc−ΔVgth" by using the sensor response threshold intensity ΔVgth determined by a concentration of a gas to be detected and a threshold input potential Vtc of the CMOS inverter. Therefore, only by setting the input setting gate potential Vin(D), a warning or an alarm can be issued for the concentration of the gas to be detected. In addition, a temperature compensation of the threshold voltage caused by a MOS structure is reduced regardless of the detection gas by setting a characteristic coefficient $\beta_R$, a threshold voltage Vtn of the n-channel field effect transistor, and the threshold voltage Vtp of the p-channel field effect transistor so as to satisfy relations "$\beta_R=1$" and "Vtp=−Vtn".

18 Claims, 16 Drawing Sheets

(58) Field of Classification Search
USPC .................................................. 73/31.06
See application file for complete search history.

(56) References Cited

U.S. PATENT DOCUMENTS

| | | | | |
|---|---|---|---|---|
| 2002/0170824 | A1* | 11/2002 | Frerichs | G01N 27/4143 204/416 |
| 2012/0217550 | A1 | 8/2012 | Usagawa | |
| 2013/0115136 | A1* | 5/2013 | Katz | G01N 27/4148 422/82.02 |
| 2013/0186178 | A1 | 7/2013 | Usagawa | |

FOREIGN PATENT DOCUMENTS

| | | |
|---|---|---|
| JP | 2009-300297 A | 12/2009 |
| JP | 2010-008371 A | 1/2010 |
| JP | 2012-073154 A | 4/2012 |
| WO | WO 2011/055605 A1 | 5/2011 |

OTHER PUBLICATIONS

Lundström, I. et al.; "Catalytic Metals and Field-effect Devices—a Useful Combination"; Sensors and Actuators; B1; pp. 15-20; (1990).

Usagawa, T. et al.; "Pt—Ti—O Gate Si-MISFET Hydrogen Gas Sensors-Devices and Packagings"; IEEE Sensors Journal, vol. 12; No. 6; pp. 2243-2248; (2012).

Miyahara, Y. et al.; "Field-effect transistor using a solid electrolyte as a new oxygen sensor"; Journal of Applied Physics; vol. 63; pp. 2431-2434; (1988).

Usagawa, T. et al.; "Device Analysis of Pt/Ti Gate Si-Metal-Oxide-Semiconductor Field-Effect Transistor Hydrogen Gas Sensors: Unintentional Oxygen Invasion into Ti Layers"; Japanese Journal of Applied Physics; vol. 51; pp. 024101-1-024101-7; (2012).

Usagawa, T. et al.; Device characteristics for Pt—Ti—O gate Si-MISFETs hydrogen gas sensors; Sensors and Actuators; vol. B160; pp. 105-114; (2011).

* cited by examiner

SEMICONDUCTOR GAS SENSOR

TECHNICAL FIELD

The present invention relates to a so-called semiconductor gas sensor which is a gas sensor using a semiconductor material, and, more particularly, the present invention relates to a technique effectively applied to a semiconductor gas sensor used for detecting hydrogen gas, hydrogen compound gas, or polar molecule gas.

BACKGROUND ART

As a gas sensor for detecting hydrogen gas or others, for example, there is a semiconductor gas sensor having a MOS (Metal-Oxide-Semiconductor) structure using a catalytic metal as a gate.

For example, Japanese Patent Application Laid-Open Publication No. 2009-300297 (Patent Document 1) discloses a gate structure which includes a Ti-modified film obtained by mixing oxygen-doped titanium containing oxygen and a titanium fine crystal, and a platinum film made by a plurality of crystal grains formed on the Ti-modified film, and in which oxygen and titanium exist in a crystal boundary region among the plurality of crystal grains.

In addition, Japanese Patent Application Laid-Open Publication No. 2012-073154 (Patent Document 2) discloses a structure which includes a gate insulating film provided on a substrate and a gate electrode provided on the gate insulating film, and in which the gate electrode has a metal-oxide mixed film obtained by mixing an oxygen-doped amorphous metal containing oxygen and an oxide crystal of the metal and a platinum film provided on the metal-oxide mixed film.

In addition, International Patent Publication WO 11/055605 (Patent Document 3) discloses a MISFET hydrogen gas sensor of low power consumption which can operate over one year by a low voltage power source. The document describes a technique in which a sensor FET is formed in a MEMS region obtained by hollowing a Si substrate of an SOI substrate, and in which a heater wiring is arranged so as to fold between a Pt—Ti—O gate and source electrode and between the Pt—Ti—O gate and drain electrode of the sensor FET.

In addition, Japanese Patent Application Laid-Open Publication No. 2010-008371 (Patent Document 4) discloses a flammable gas sensor which includes a sensor chip, a stem on which the sensor chip is mounted, and a metal cap having an upper portion and a side portion and having the bottom of the side portion welded to the peripheral of the stem, and in which the sensor chip is surrounded by the stem and the metal cap.

PRIOR ART DOCUMENTS

Patent Documents

Patent Document 1: Japanese Patent Application Laid-Open Publication No. 2009-300297
Patent Document 2: Japanese Patent Application Laid-Open Publication No. 2012-073154
Patent Document 3: International Patent Publication WO 11/055605
Patent Document 4: Japanese Patent Application Laid-Open Publication No. 2010-008371

SUMMARY OF THE INVENTION

Problems to be Solved by the Invention

Until now, a semiconductor gas sensor which continuously measures a gas concentration of hydrogen gas, hydrogen compound gas, or polar molecule gas has been proposed. However, while it is required to continuously recognize the gas concentration, practically, information of the gas concentration in one, two or more setting ranges is required in many cases. That is, it is desired to provide a semiconductor gas sensor having a simple structure and being easily operate which can detect one, two or more specified gas concentrations and can correctly issue a warning or an alarm.

The present invention provides a semiconductor gas sensor which can detect one, two or more specified gas concentrations for hydrogen gas, hydrogen compound gas, or polar molecule gas, and can correctly issue a warning or an alarm.

In addition, the present invention provides a semiconductor gas sensor which can detect a designated gas concentration only by changing an input setting.

In addition, the present invention provides a semiconductor gas sensor which reduces temperature compensation (drift or variation) of a threshold voltage caused by a MOS structure regardless of the detection gas.

The above and other objects and novel characteristics of the present invention will be made apparent from the present specification and the accompanying drawings.

Means for Solving the Problems

In order to solve the above-described problems, a semiconductor gas sensor of the present invention includes a CMOS inverter which is configured by an n-channel field effect transistor having a catalytic gate and a p-channel field effect transistor having a catalytic gate. An input setting gate voltage Vin(D) of the CMOS inverter is set to satisfy "Vin(D)=Vtc−ΔVgth" by using a sensor response threshold intensity ΔVgth determined by a gas concentration which is desirably detected and a threshold input voltage Vtc of the CMOS inverter.

Effects of the Invention

According to the present invention, it is possible to provide a semiconductor gas sensor which can detect one, two or more specified gas concentrations for hydrogen gas, hydrogen compound gas, or polar molecule gas, and can correctly issue a warning or an alarm.

In addition, according to the present invention, it is possible to provide a semiconductor gas sensor which can detect a designated gas concentration only by changing an input setting.

In addition, according to the present invention, it is possible to provide a semiconductor gas sensor which reduces temperature compensation (drift or variation) of a threshold voltage caused by a MOS structure regardless of the detection gas.

Problems, configurations, and effects other than those described above will become apparent through the explanation on the following embodiments.

BRIEF DESCRIPTIONS OF THE DRAWINGS

Figure 16:
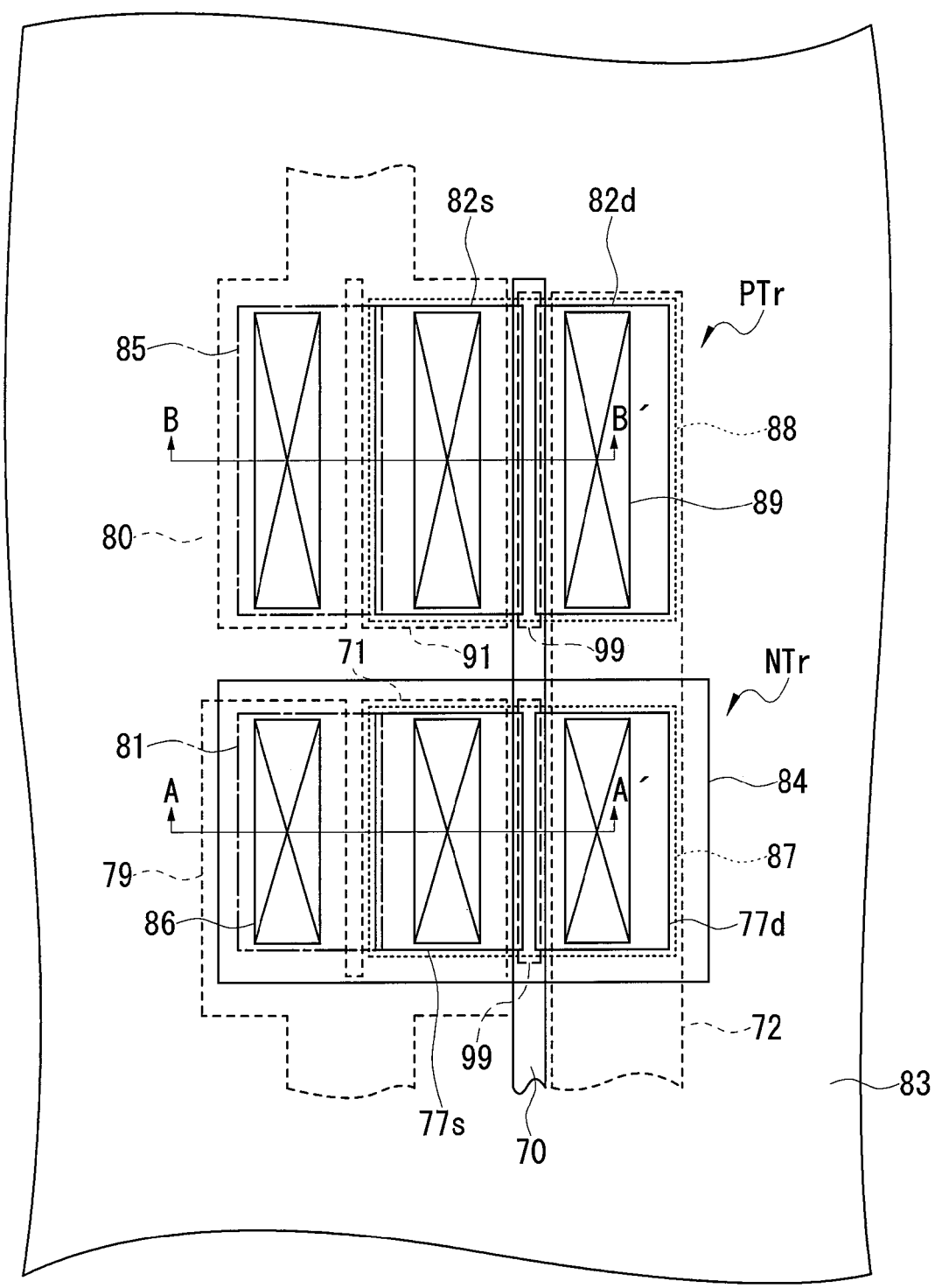
FIG. 16 is one example of a plan view of a CMOS inverter according to the fourth embodiment.
Figure 17:
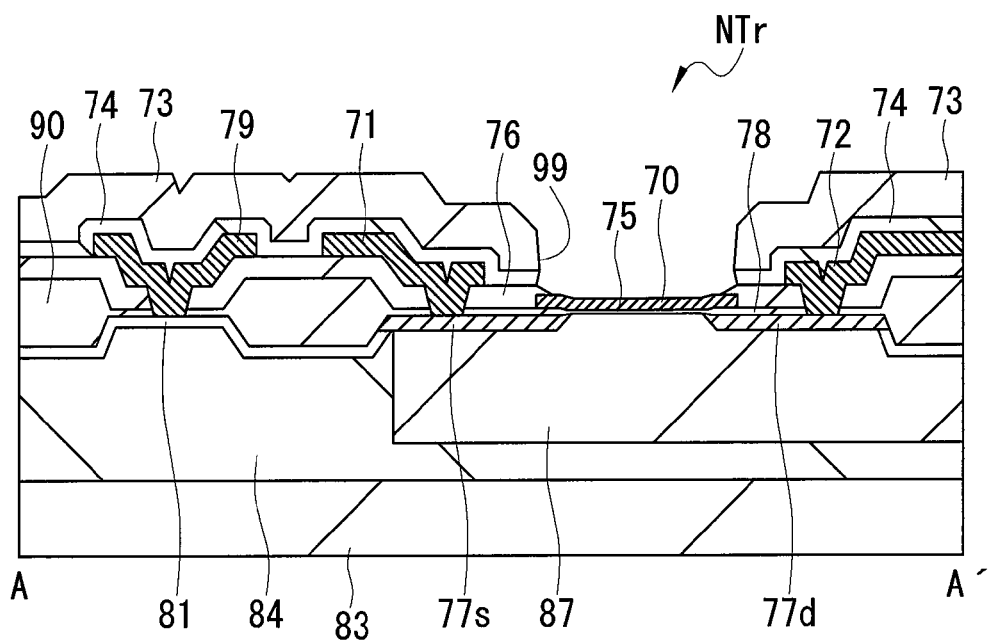
Figure 18:
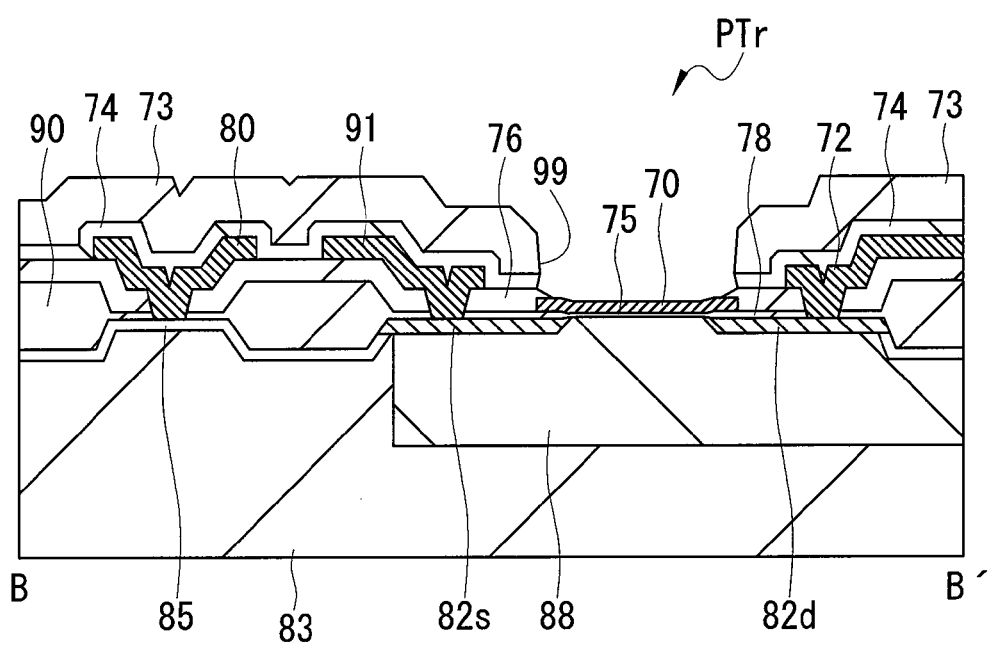

FIG. 17 is a cross-sectional view of a principal part of an nMOS transistor configuring the CMOS inverter according to the fourth embodiment (a cross-sectional view of a principal part thereof taken along a line A-A' of FIG. 16); and FIG. 18 is a cross-sectional view of a principal part of a pMOS transistor configuring the CMOS inverter according to the fourth embodiment (a cross-sectional view of a principal part thereof taken along a line B-B' of FIG. 16).

DETAILED DESCRIPTION OF PREFERRED EMBODIMENTS

In the embodiments described below, the invention will be described in a plurality of sections or embodiments when required as a matter of convenience. However, these sections or embodiments are not irrelevant to each other unless otherwise stated, and the one relates to the entire or a part of the other as a modification example, details, or a supplementary explanation thereof.

Also, in the embodiments described below, when referring to the number of elements (including number of pieces, values, amount, range, and the like), the number of the elements is not limited to a specific number unless otherwise stated or except the case where the number is apparently limited to a specific number in principle. The number larger or smaller than the specified number is also applicable.

Further, in the embodiments described below, it goes without saying that the components (including element steps) are not always indispensable unless otherwise stated or except the case where the components are apparently indispensable in principle.

Also, when "formed of A", "formed by A", "having A" or "including A" is described, it goes without saying that other components are not eliminated unless otherwise specified to be only the component. Similarly, in the embodiments described below, when the shape of the components, positional relation thereof, and the like are mentioned, the substantially approximate and similar shapes and the like are included therein unless otherwise stated or except the case where it is conceivable that they are apparently excluded in principle. The same goes for the numerical value and the range described above.

Also, in some drawings used in the following embodiments, hatching is used even in a plan view so as to make the drawings easy to see in some cases. Also, in the following embodiments, a MOSFET (Metal Oxide Semiconductor Field Effect Transistor) representing a field effect transistor is referred to as MOS transistor, a p-channel type MOSFET is abbreviated as "pMOS", and an n-channel type MOSFET is abbreviated as "nMOS".

In addition, in the following embodiments, a semiconductor gas sensor will be referred to as a gas sensor, a gate having a catalysis will be referred to as a catalytic gate, and a CMOS inverter having the gate having the catalysis will be referred to as a catalytic gate CMOS inverter.

Also, components having the same function are denoted by the same reference symbols throughout all the drawings for describing the following embodiments, and the repetitive description thereof will be omitted. Hereinafter, the present embodiment will be described in detail based on the drawings.

The present embodiment relates to a sensing technique of the gas sensor, and hydrogen gas, hydrogen compound gas, or polar molecule gas is assumed as the type of the gas. They are different from each other in a gas detection mechanism but the same as each other in that the gas concentration is detected by extracting a shift amount of a threshold voltage as a sensor signal. The gas detection mechanism is determined by the gas type and a nature of the catalytic gate structure.

In the case of the hydrogen gas, hydrogen molecules are dissociated into hydrogen atoms by the catalysis of the catalytic gate, and the gas concentration is detected by the shift amount of the threshold voltage caused by a hydrogen-induced dipole formed on a boundary surface between the catalytic gate and a gate insulating film.

In the case of the hydrogen compound gas, hydrogen atoms are dissociated from hydrogen compound molecules (to be ammonia, hydrogen sulfide, etc.) by the catalysis of the catalytic gate, and the gas concentration is detected by the same sensing principle as the case of the hydrogen gas.

In the case of the polar molecule gas, the catalytic gate structure using a nano-composite structure or others is used. The polar molecules (for example, ethanol, ammonia, etc.) are adsorbed to a nano-scale capacitive coupling gate structure, and polarize, so that the threshold voltage is changed. The gas concentration is detected from the shift amount of the threshold voltage at this time. In a lot of polar molecules (the molecule itself has a dipole moment), the hydrogen atoms cannot be dissociated by the catalysis. However, in ethanol or ammonia, the hydrogen atoms can be dissociated. In a case having both natures of ethanol or ammonia, the molecules polarize after the adsorption, and therefore, there is a high possibility of occurrence of the shift of the threshold voltage because of the both sensing mechanisms even whether the sensor signal is strong or weak.

First, since the gas sensor according to the embodiment may be clear, the structures of various gas sensors for detecting the hydrogen gas studied by the present inventor and the problems to be solved by the various gas sensors found out by the present inventor will be described in detail.

As the gas sensor for detecting the hydrogen gas, a Si(silicon)-MOSFET (Metal-Oxide-Semiconductor Field Effect Transistor) gas sensor having a Pd gate structure using a catalytic metal (such as Pd (palladium)) for the gate is cited (for example, see Applied Physics Letters, Lundstrom et al., Vol 26, No 2, 15 (1975) 55 to 57).

In this Si-MOSFET gas sensor having the Pd gate structure, the sensing principle for detecting the hydrogen gas is proposed, for example, as follows. First, the hydrogen molecules are dissociated on a surface of a Pd gate by the catalysis, the hydrogen atoms (or protons) are diffused and moved to a boundary surface between the Pd gate and the gate insulating film. Then, a proton-electron pair polarized to have the dipole moment (in a separation state of the gravity centers of the proton and the electron) is formed in vicinity of the boundary surface between the Pd gate and the gate insulating film. Therefore, the threshold voltage of the Si-MOSFET gas sensor having the Pd gate structure is shifted. By using such a phenomenon, the hydrogen gas concentration can be detected.

Currently, application of a MOSFET gas sensor using the catalytic metal such as Pd or Pt (platinum) for the gate to gas other than the hydrogen gas such as hydrogen compound gas or polar molecule gas has been also studied (see, for example, Sensors and Actuators, I. Lundstrom, B1 (1990) 15 to 20). Furthermore, in order to improve the reliability of the MOSFET gas sensor using Pd or Pt for the gate, a MISFET (Metal-Insulation-Semiconductor Field Effect Transistor) gas sensor having a Pt—Ti—O gate structure using Pt—Ti—O (Platinum-Titan-Oxide) for the gate has been proposed (see, for example, Patent Document 1 described above). Here, the MIS is the abbreviation of Metal-Insulation-Semiconductor and is a high-level concept of the MOS.

In the case of the hydrogen gas, when the absolute value (hereinafter, referred to as a sensor response intensity) of the shift amount of a threshold voltage Vth of the MOSFET gas sensor is expressed as $\Delta Vg$, the sensor response intensity $\Delta Vg$ can be expressed as follows so as to reflect the dissociation and adsorption of the surface of the gate metal having the catalysis of the hydrogen molecules.

$$\Delta Vg = \Delta Vg_{max} \times \sqrt{(C/C_0)}/(1+\sqrt{(C/C_0)})  \quad \text{Expression (1)}$$

Here, "$\Delta Vg_{max}$" represents a maximum value of the sensor response intensity $\Delta Vg$, "$C$" represents a hydrogen gas concentration in vicinity of the gas sensor, and "$C_0$" represents a hydrogen concentration obtained when occupying the half of a hydrogen adsorption site of the gas sensor (see, for example, IEEE Sensors Journal, T. Usagawa et al., 12 (2012) 2243 to 2248). Therefore, the hydrogen gas concentration can be detected by measuring the sensor response intensity $\Delta Vg$.

In addition, even in the case of the polar molecule gas such as ethyl alcohol having the polarity, the sensing principle for detecting the polar molecule gas is slightly different from Expression (1). However, as similar to the case of the hydrogen gas, the polar molecule gas concentration can be detected from the sensor response intensity $\Delta Vg$ of the MOSFET gas sensor (see, for example, Patent Document 2).

In addition, not only the MOS transistor but also a MIS capacitor (Metal-Insulation-Semiconductor capacitor) is also applied as the structure of the gas sensor. In addition, as the semiconductor material, application of not only a Si semiconductor but also a SiC (silicon carbide) semiconductor, a GaAs (gallium arsenide) semiconductor, a GaN (gallium nitride), and a diamond (carbon) semiconductor or others are studied. In addition, the application of a thin film transistor (see, for example, Patent Document 3) on a glass substrate is also studied.

Incidentally, for the detection of the gas concentration in the MOSFET gas sensor, an information process which amplifies and outputs a small voltage signal and converts the signal into a gas concentration is used. For example, a method is used, the method obtaining the sensor response intensity $\Delta Vg$ by using a so-called voltage follower circuit which applies a constant voltage to the gate of the MOSFET gas sensor to cause a constant voltage and a constant current flow between the drain and the source and measuring the output of the circuit (see, for example, J. Appl. Phys., Y. Miyahara, FIG. 2 in 63 (1988) 2431 to 2434).

That is, in the MOSFET gas sensor which has been proposed until now, the gas concentration is determined by (1) converting the gas concentration into an electric signal (a voltage signal in many cases), (2) amplifying the electric signal if the electric signal is small, (3) taking the gas concentration as analog data (a continuous amount), and (4) converting the analog data into digital data by an AD converter. Note that a mechanism to detect the gas concentration is the same in any above-described gas sensor having the MOS (or MIS) structure. In addition, the sensor signal is also detected by using the similar analog circuit.

However, in practical needs, while it is required to correctly and continuously recognize the gas concentration, the information of the gas concentration classified into groups in a certain range is required in many cases.

Practically, a gas sensor for a gas having a possibility of gas explosion has a standard for installation of the gas sensor, which issues an alarm (with red lamp+voice sound) at 25% or lower of the explosion lower limit concentration and issues a warning (with red lamp flickering) at about 1% of the explosion lower limit concentration. When the gas sensor is used as an alarm, the less the issuance of such a "false alarm" as issuing the alarm in spite of a fact that the gas concentration does not reach the explosion lower limit is, the more the gas sensor is good.

In addition, as a specification example of the hydrogen gas sensor required for a hydrogen gas station, five-level grouping of (1) a warning level of 500 ppm hydrogen leakage, (2) a normal usage upper limit of 0.1%, (3) a system warning level of 0.5%, (4) a system power off level of 1%, and (5) station power off level of 5%, or others, is proposed.

In this specification, the explosion lower limit concentration of the hydrogen gas is 4.0% under 1 atmosphere pressure, (1) the warning level of 500 ppm hydrogen leakage corresponds to issuance of a warning at about 1% of the explosion lower limit concentration of a gas alarm installation manual, and (4) the system power off level of 1% corresponds to an alarm at 25% or less thereof. A reason why the multiple levels are prepared as the standard as described above is that specific countermeasures are changed depending on a range of the gas concentration.

However, a gas sensor has not been developed yet, the gas sensor having a simple configuration and easily operating so that the gas concentration for the hydrogen gas, hydrogen compound gas, or polar molecule gas can be detected in one, two or more setting ranges, and then, a warning or an alarm can be issued. It can be expected that the sensor system is simplified by using such a gas sensor.

Also, in the MOSFET gas sensor, a drift phenomenon of the threshold voltage appears. As a solution, it is considered that a differential circuit is effective. For example, a differential circuit system is proposed, the differential circuit system cancelling a change of the threshold voltage not depending on the detection gas by using a reference element having no response to the gas and by making a difference between the output of the sensor element and the output of the reference element. By this system, a change of an external environmental temperature of the MOSFET gas sensor and the change of the sensor temperature can be compensated in the temperatures. However, by this system, a variation caused by a difference in the structure between the sensor element and the reference element cannot be reduced.

The problems are summarized below.

As a first problem, a gas sensor has not been developed yet, the gas sensor being capable of detecting one, two or more specific gas concentrations for the hydrogen gas, hydrogen compound gas, or polar molecule gas, and capable of issuing a warning or an alarm.

As a second problem, a gas sensor has not been developed yet, the gas sensor being capable of detecting a designated gas concentration only by changing the input setting.

As a third problem, a problem of the temperature compensation (drift or variation) of the threshold voltage caused by not the detection gas but the MOS structure is not solved.

Hereinafter, specific characteristics and structure of the gas sensor will be described in detail through embodiments.

First Embodiment

Figure 1:
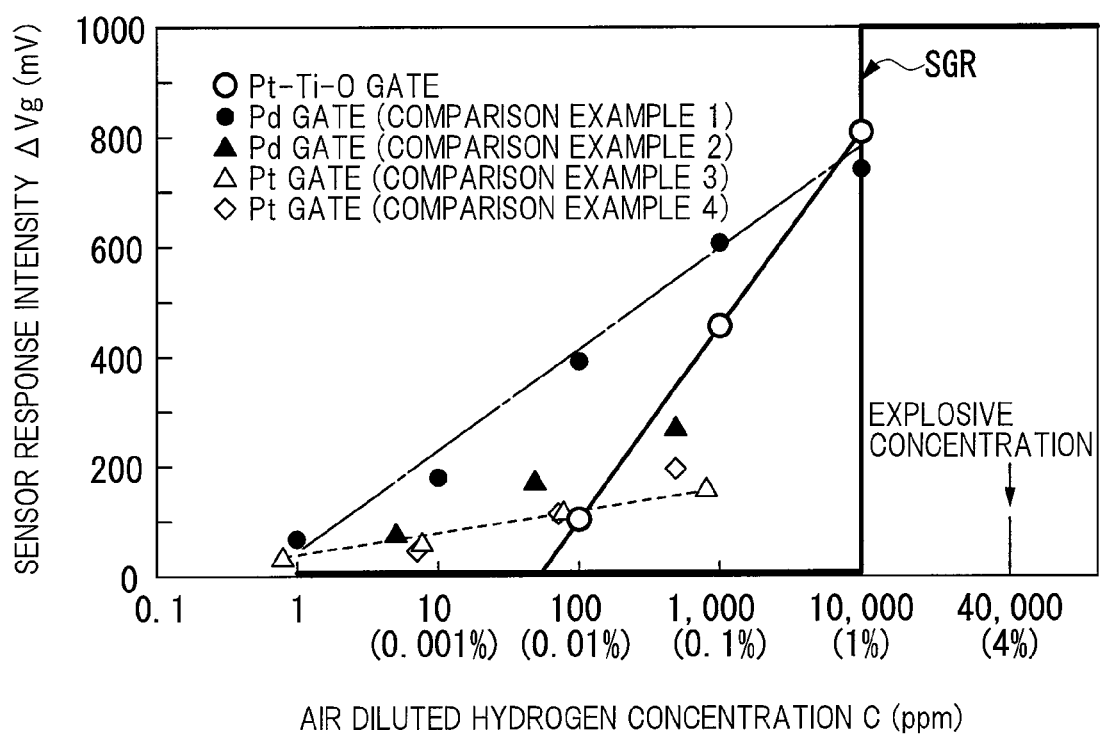
FIG. 1 is a graph summarizing experimental data of a response intensity (ΔVg) with respect to an air-diluted hydrogen concentration (C) in a Si-MOSFET gas sensor according to a first embodiment.

FIG. 1 illustrates a graph summarizing experimental data of the sensor response intensity ($\Delta Vg$) with respect to an air-diluted hydrogen concentration (C) in the Si-MOSFET gas sensor. Here, the sensor response intensity is an absolute value of the shift amount of the threshold voltage.

in a Si-MOSFET gas sensor having the Pt—Ti—O gate structure, the sensor response intensity $\Delta Vg$ can be approximated with a high accuracy by Expression (2) obtained in a range of "$0.1 \leq C/C_0 \leq 10$" from Langmuir formula of Expression (1).

$$\Delta Vg(V) = 0.355 \log C(\text{ppm}) - 0.610 \quad \text{Expression (2)}$$

Examples of $\Delta Vgmax$ and $C_0$ of the Langmuir formula of Expression (1) are summarized in Table 1. Expression (2) shows that a physical phenomenon can be reproduced with a high accuracy by the Langmuir formula of Expression (1).

TABLE 1

|  | $\Delta Vgmax$ (mV) | $C_0$ (ppm) | Hydrogen concentration range (ppm) |
|---|---|---|---|
| Pt—Ti—O gate | 1365 | 4388.0 | 100 to 10000 |
| Pd gate (comparative example 1) | 830 | 130.0 | 1 to 10000 |
| Pd gate (comparative example 2) | 377 | 68.6 | 5 to 500 |
| Pd gate (comparative example 3) | 194 | 30.1 | 8 to 800 |
| Pd gate (comparative example 4) | 333 | 229.0 | 7 to 500 |

The $\Delta Vgmax$ and $C_0$ in the Pt—Ti—O gate structure shown in Table 1 are guided by regarding the Expression (1) and the Expression (2) so as to be equal to each other in a range of "$0.1 \leq C/C_0 \leq 10$". It is needless to say that the values shown in Table 1 are an example, and that the values are changed depending on a specific Pt—Ti—O gate structure.

As illustrated in FIG. 1, such a point that rising of the sensor response intensity $\Delta Vg$ with respect to the air-diluted hydrogen concentration C is rapid shows a high sensitivity and a high intensity the Pt—Ti—O gate structure, and this point is a difference from the Si-MOSFET gas sensor having the Pt gate structure and the Pd gate structure. The fact that $\Delta Vgmax$ and $C_0$ of the Pt—Ti—O gate structure shown in Table 1 are higher than $\Delta Vgmax$ and $C_0$ of other structure supports the high sensitivity and the high intensity of the Pt—Ti—O gate structure.

For example, in a case of a hydrogen gas whose hydrogen concentration is in the explosion concentration region at 4% (40,000 ppm), the alarm can be issued for the explosion concentration if the concentration is exactly detected at 1% concentration (10,000 ppm) obtained by reducing 4% concentration (40,000 ppm) by 25%. That is, as a step-type gas response SGR illustrated by a thick solid line in FIG. 1, such response characteristics as showing no response until the concentration becomes 1%, rapidly rising at 1% concentration as the threshold value, and showing a constant voltage at 1% concentration or larger. In the SGR illustrated in FIG. 1, 1.0 V is exemplified. However, it is needless to say that this value is arbitrary, and the step function may be a dropping type.

If the warning is issued when the hydrogen concentration is 0.05% (500 ppm), it is only required to set the hydrogen concentration at the rising of the step-type gas response SGR illustrated by the thick solid line in FIG. 1 to a concentration of 0.05%. It is only required to prepare two gas sensors in order to issue the warning and the alarm at two points. In the case of the semiconductor device, it is only required to integrate two types of gas sensors in the same chip.

Meanwhile, the nMOS transistor has been used in the Si-MOSFET gas sensor. However, similarly, the pMOS transistor can be used. That is, if the gate structure of the pMOS transistor is the same as the gate structure of the nMOS transistor, the control mechanism and the hydrogen response mechanism of the threshold voltage of the Si-MOSFET gas sensor can also be understood by a sensor model based on the dipole moment (see Japanese Journal of Applied Physics, T. Usagawa et al., Vol 51 (2012) 024101-1 to 024101-7, and Sensors and Actuators, T. Usagawa et al., B160 (2011) 105 to 114). According to these experiments, it can be seen that the sensor response intensity $\Delta Vg$ hardly depends on the flat structure (gate length and gate width) of the MOS transistor. In the present embodiment, the gate structure means a structure up to a semiconductor boundary surface in the cross section of the gate region of the MOS transistor.

As illustrated in FIG. 1, the gas sensor according to the first embodiment has such a feature that the gas sensor is configured by the MOS transistor having the gate having the rising of the step-type gas response SGR whose sensor response intensity ΔVg rapidly increases at a predetermined gas concentration. Furthermore, the gas sensor according to the first embodiment has such a feature that the gas sensor is of the CMOS (Complementary Metal Oxide Semiconductor; complementary metal-oxide film-semiconductor) type which is configured by the nMOS transistor and the pMOS-FET in order to avoid the drift phenomenon of the threshold voltage.

Figure 2:
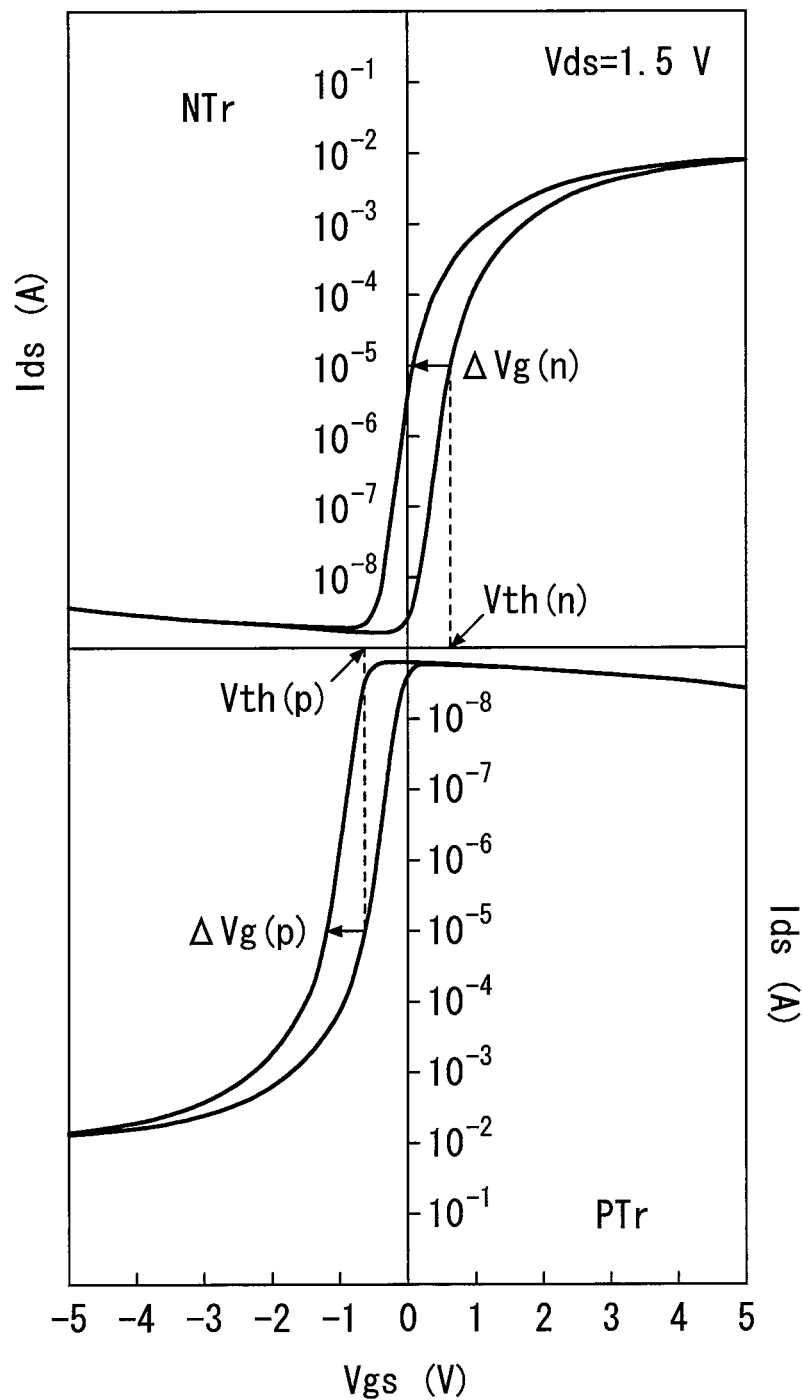
FIG. 2 is a graph illustrating an example of the I-V characteristics of an nMOS transistor and a pMOS transistor having a Pt—Ti—O gate structure with respect to a 0.1% hydrogen irradiation according to the first embodiment.
Figure 3:
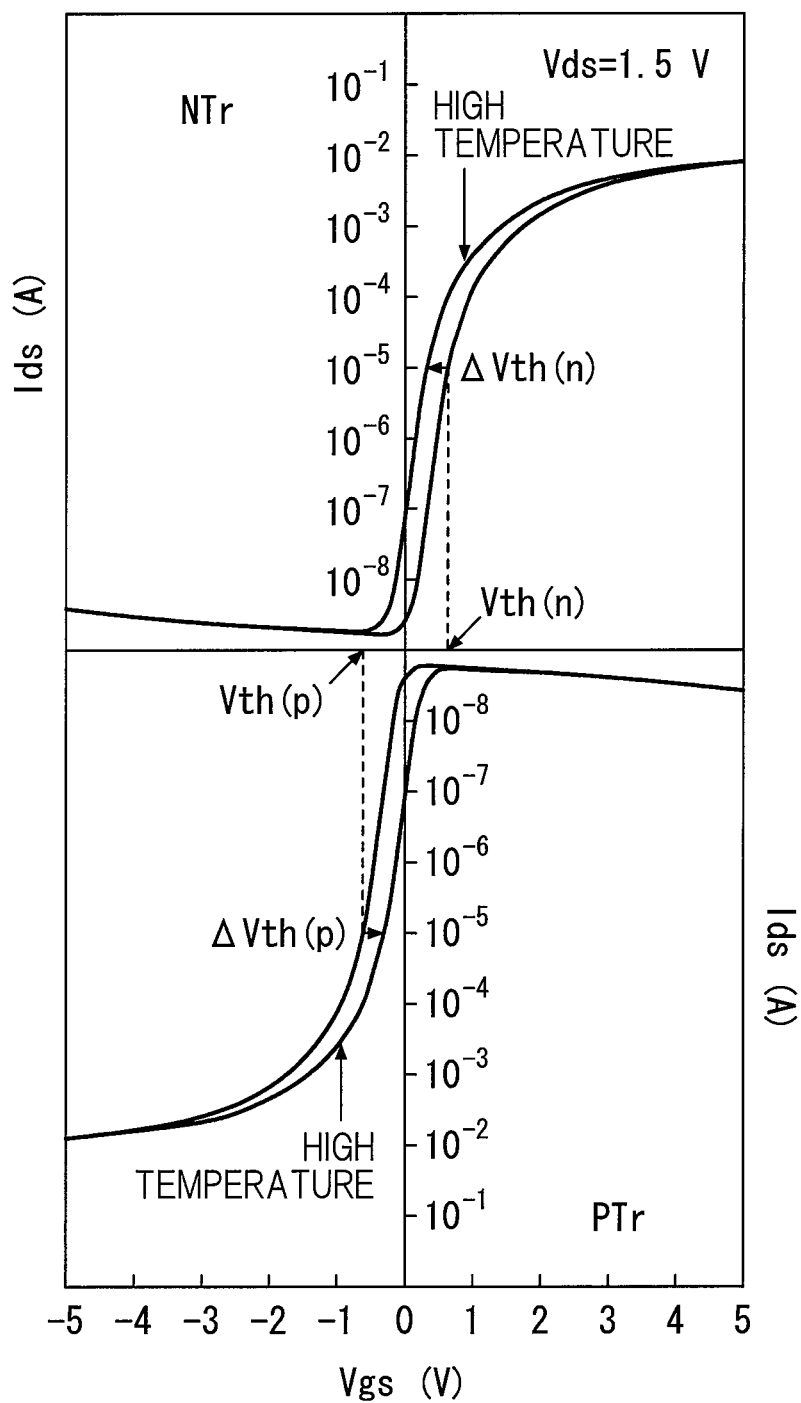
FIG. 3 is a graph illustrating an example of the I-V characteristics of the nMOS transistor and the pMOS transistor having the Pt—Ti—O gate structure measured at a room temperature (about 24° C.) and a high temperature (115° C.) according to the first embodiment.

First, the I-V characteristics (current-voltage characteristics) of the nMOS transistor and the pMOS transistor having the Pt—Ti—O gate structure will be described. FIG. 2 is a graph illustrating an example of the I-V characteristics (current-voltage characteristics) of the nMOS transistor and the pMOS transistor having the Pt—Ti—O gate structure with respect to a 0.1% hydrogen irradiation. FIG. 3 is a graph illustrating an example of the I-V characteristics of the nMOS transistor and the pMOS transistor having the Pt—Ti—O gate structure measured at a room temperature (about 24° C.) and a high temperature (115° C.). In FIGS. 2 and 3, the horizontal axis represents a source-gate voltage (Vgs), and the vertical axis represents a source-drain current (Ids). In this case, the source-drain voltage (Vds) of the nMOS transistor is 1.5 V, and the source-drain voltage (Vds) of the pMOS transistor is −1.5 V.

In FIG. 2, the threshold voltage of the nMOS transistor and the threshold voltage of the pMOS transistor are respectively denoted by Vth(n) and Vth(p), and the parallel shift of the I-V characteristics at the time of the hydrogen irradiation is indicated by an arrow. In addition, the shift amount of the threshold voltage of the nMOS transistor and the shift amount of the threshold voltage of the pMOS transistor are respectively denoted by ΔVg(n) and ΔVg(p).

In FIG. 3, the threshold voltage of the nMOS transistor and the threshold voltage of the pMOS transistor are denoted by Vth(n) and Vth(p), respectively, and the parallel shift of the I-V characteristics caused when the temperature is changed from a room temperature (about 24° C.) to a high temperature (115° C.) is indicated by an arrow. In addition, the shift amount of the threshold voltage of the nMOS transistor and the shift amount of the threshold voltage of the pMOS transistor are denoted by ΔVth(n) and ΔVth(p), respectively.

As illustrated in FIG. 2, with respect to the hydrogen irradiation, both of a threshold voltage Vth(n) of the nMOS transistor and a threshold voltage Vth(p) of the pMOS transistor are shifted in parallel in a negative direction (the left direction of FIG. 2) on a point of the source-gate voltage (Vgs) by the same value (ΔVg(n)=ΔVg(p)) (in-phase change). In the gate structure of the nMOS transistor and the gate structure of the pMOS transistor, a channel, a gate length, and a gate width are designed so that function forms of the I-V characteristics are almost the same. However, since the gate structures except for them are the same as each other, the phenomenon at the time of the hydrogen irradiation can be explained by using the physics of the MOSFET gas sensor.

On the other hand, as illustrated in FIG. 3, when the temperature is increased from a room temperature (about 24° C.) to a high temperature (115° C.), the threshold voltage Vth(n) of the nMOS transistor is shifted in parallel in the negative direction (the left direction of FIG. 3) on a point of the source-gate voltage (Vgs) by ΔVth(n), and the threshold voltage Vth(p) of the pMOS transistor is shifted in parallel in a positive direction (the right direction of FIG. 3) on a point of the source-gate voltage (Vgs) by ΔVth(p) (anti-phase change). The ΔVth(n) and the ΔVth(p) have almost the same value as each other. Physically, when the temperature is increased, the source-drain currents Ids in both of the nMOS transistor and the pMOS transistor are increased. In general, in the MOS structure, the temperature changes of the threshold voltage Vtn of the nMOS transistor and the threshold voltage Vtp of the pMOS transistor in the vicinity of a reference temperature T0 are expressed as follows.

$$Vtn = Vtn0 - Kn(T - T0) \qquad \text{Expression (3)}$$

$$Vtp = Vtp0 + Kp(T - T0) \qquad \text{Expression (4)}$$

The Vtn0 and the Vtp0 are the threshold voltages at the time of the reference temperature T0, and the Kn and the Kp in the vicinity of the reference temperature are expressed as follows.

$$Kn \approx Kp = 2 \text{ to } 3 \text{ mV/}° \text{C.} \qquad \text{Expression (5)}$$

Although specific values of the Kn and the Kp depend on the semiconductor materials such as Si, SiC, and GaC (gallium carbide) or diamond (carbon), the temperature characteristics of the threshold voltages Vtn and Vtp and a relation of Kn≅Kp are maintained.

Figure 4:
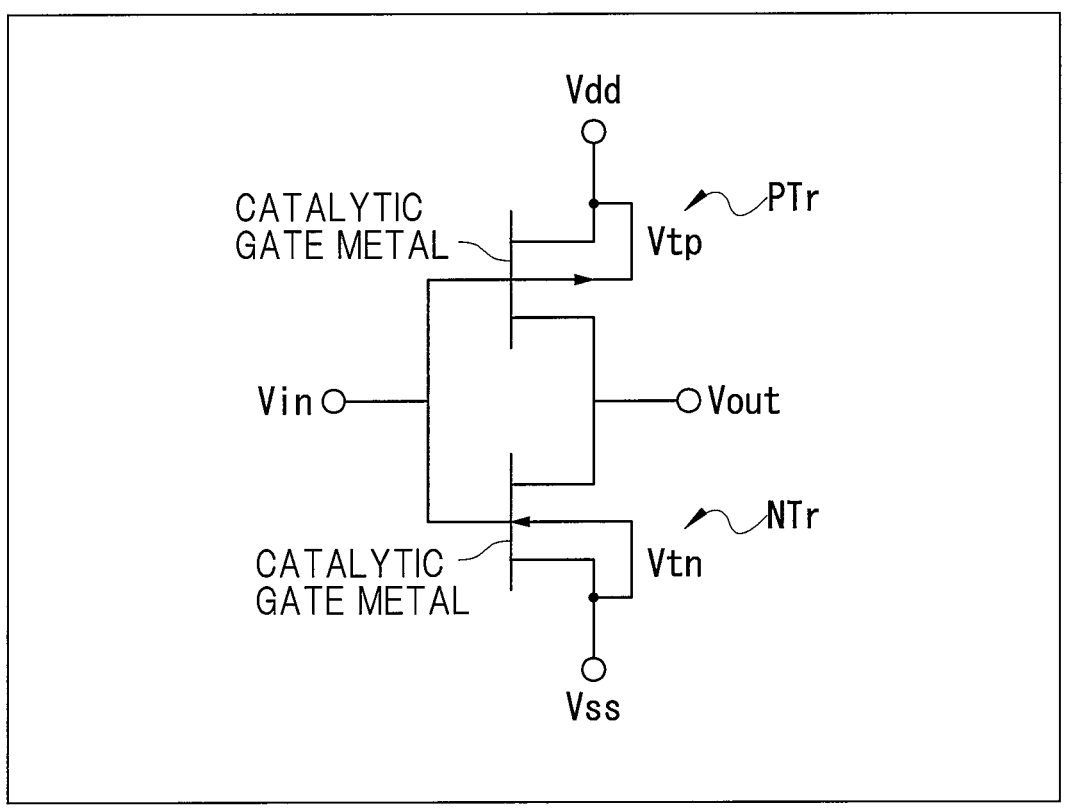
FIG. 4 is a circuit diagram illustrating a CMOS inverter which includes a gate having a catalysis according to the first embodiment.

Next, the CMOS inverter which includes the gate having the catalysis will be described by using FIG. 4. FIG. 4 is a circuit diagram illustrating the CMOS inverter which includes the gate having the catalysis.

In the catalytic gate CMOS inverter, a load formed by an enhancement-type pMOS transistor PTr and a driver formed by an enhancement-type nMOS transistor NTr are arranged so as to be complementary (logic inverting circuit). The Vdd represents a high potential, the Vss represents a low potential, the Vin represents an input potential, the Vout represents an output potential, the Vtp represents a threshold voltage of the pMOS transistor, and the Vtn represents a threshold voltage of the nMOS transistor. In the inverter, the high potential Vdd is generally set to have a voltage difference higher than the low potential Vss by about 3 to 24 V. In general, the high potential Vdd is a power supply voltage, and the low potential Vss is a ground voltage.

When the input potential Vin is at the same potential as the low potential Vss, the pMOS transistor is turned on, and the nMOS transistor is turned off. Therefore, the output potential Vout is almost equal to the high potential Vdd. In addition, when the input potential Vin is at the same potential as the high potential Vdd, the pMOS transistor is turned off, and the nMOS transistor is turned on. Therefore, the output potential Vout is almost equal to the low potential Vss. In other words, the opposite voltage to the input potential Vin appears on the output potential Vout.

Figure 5:
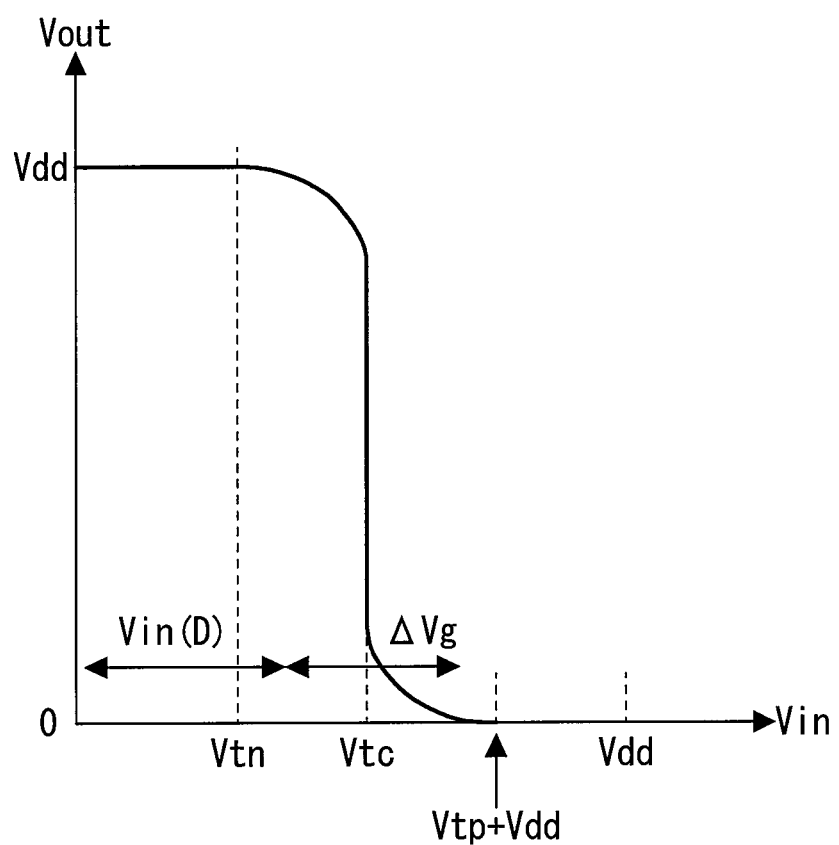
FIG. 5 is a graph illustrating logical inversion characteristics of an output potential (Vout) with respect to an input potential (Vin) of the CMOS inverter according to the first embodiment.

Next, the operation principle of the CMOS will be quantitatively described by using FIG. 5. FIG. 5 is a graph illustrating logical inversion characteristics of the output potential (Vout) with respect to the input potential (Vin) of the CMOS inverter. The threshold voltage of the nMOS transistor and the threshold voltage of the pMOS transistor will be denoted by Vtn and Vtp, respectively. The explanation will be made on assumption that the low potential Vss is 0 V. However, the low potential is not limited thereto.

When it is assumed that a gate length is "Lg(n)", a gate width is "Wg(n)", a gate capacity per unit area is "COx(n)", an n-channel effective electron mobility is "μn", and a characteristic coefficient is "βn", the I-V characteristics in a saturation region of the nMOS transistor in the CMOS inverter are expressed as follows.

$$Ids=\beta n(Vin-Vtn)^2/2 \quad \text{Expression (6)}$$

$$\beta n=Wg(n)\mu nCOx(n)/Lg(n) \quad \text{Expression (7)}$$

When it is assumed that a gate length is "Lg(p)", a gate width is "Wg(p)", a gate capacity per unit area is "COx(p)", a p-channel effective hole mobility is "µp", and a characteristic coefficient is "βp", the I-V characteristics in the saturation region of the pMOS transistor in the CMOS inverter is expressed as follows in the pMOS transistor serving as the load of this CMOS inverter.

$$Ids=\beta p(Vin-Vdd-Vtp)^2/2 \quad \text{Expression (8)}$$

$$\beta p=Wg(p)\mu pCOx(p)/Lg(p) \quad \text{Expression (9)}$$

In such consideration that Expression (6) and Expression (8) are equal to each other and the high potential Vdd is larger than a threshold input potential Vtc (Vdd>Vtc), the threshold input potential Vtc of the logical inversion characteristics is expressed as follows.

$$Vtc=[Vdd+\sqrt{(\beta_R)}Vtn+Vtp]/(1+\sqrt{(\beta_R)}) \quad \text{Expression (10)}$$

Here, "abs" is a symbol indicating an absolute value signal, and the following Expression is established.

$$\beta_R=\beta n/\beta p \quad \text{Expression (11)}$$

Here, gate lengths Lg (n) and Lg (p), gate widths Wg (n) and Wg (p), and gate capacities per unit area COx(n) and COx(p) represent are design parameters. If the n-channel effective electron mobility "µn" and the p-channel effective hole mobility "µp" can be measured, the threshold input potential Vtc of the logical inversion characteristics can be designed.

For example, a relation of "Vtc=Vdd/2" is established in a case of "$\beta_R=1$" and "Vtp=-Vtn", and the symmetry becomes most preferable. The pMOS transistor and the nMOS transistor are of an enhancement type, the threshold voltage Vtp of the pMOS transistor has a negative value, and the threshold voltage Vtn of the nMOS transistor has a positive value.

The gas sensor according to the first embodiment has a structure in which the catalytic metal for detecting the hydrogen gas, hydrogen compound gas, or polar molecule gas is used for the gate of each of the pMOS transistor and the nMOS transistor configuring the CMOS inverter, and in which the gate on the channel directly contacts on the gas environment.

First, an operation principle of a catalytic gate CMOS gas sensor will be described by using FIGS. 5, and 6 to 8 described above, and then, a specific structure of the catalytic gate CMOS gas sensor will be described by using FIGS. 9 to 11.

Figure 6:
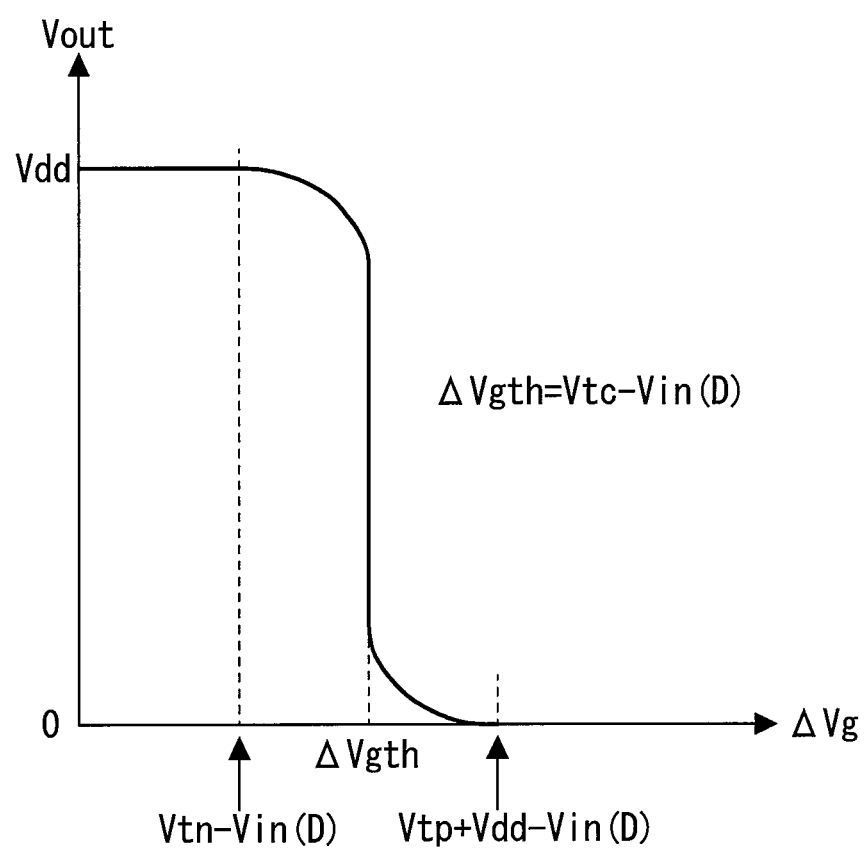
FIG. 6 is a graph illustrating logical inversion characteristics of the output voltage (Vout) with respect to a sensor response intensity (ΔVg) of the CMOS inverter according to the first embodiment.

The operation principle of the catalytic gate CMOS gas sensor according to the first embodiment will be described by using FIGS. 5 and 6. FIG. 6 is a graph illustrating logical inversion characteristics of the output potential (Vout) with respect to the sensor response intensity (ΔVg) of the CMOS inverter.

When the catalytic gate of the pMOS transistor and the catalytic gate of the nMOS transistor are exposed to a detecting target gas such as hydrogen gas, hydrogen compound gas, or polar molecule gas, the threshold voltage Vtp of the pMOS transistor is shifted in the negative direction, and the threshold voltage Vtn of the nMOS transistor is also shifted in the negative direction in accordance with the gas concentration (in-phase change). If the gate structures (the catalytic gate and the gate insulating film) are designed to be the same as each other, the sensor response intensity ΔVg becomes the same in both structures. If the materials and the structures of the gate insulating films are the same as each other, the sensor response intensities ΔVg are almost the same as each other in both structures as long as the catalytic gates are the same as each other even when the thicknesses of the gate insulating films contacting on the semiconductor are changed more or less.

The exposure of the detection target gas such as the hydrogen gas, hydrogen compound gas, or polar molecule gas to each catalytic gate of both of the nMOS transistor and the pMOS transistor of the CMOS inverter (see FIG. 4) is equivalent to the fact that the sensor response intensity ΔVg corresponding to the gas concentration is actually applied to the catalytic gate of the CMOS inverter. And, the catalytic gate CMOS inverter is operated so that the input potential becomes (Vin+ΔVg).

In other words, as illustrated in FIG. 5, when the input potential Vin is set to an input setting gate potential (an initial value of the input potential Vin) Vin(D) (Vin<Vtc) to increase the exposed gas concentration, the CMOS inverter can be converted when "(Vin(D)+ΔVg)" exceeds the threshold input potential Vtc. In other words, as increasing the exposed gas concentration from the initial state of the CMOS inverter without the detection target gas (from "Vin=Vin(D)"), the sensor response intensity ΔVg is gradually increased, and the output potential Vout is inverted under a gas environment with a certain threshold concentration, so that a relation of "Vout=Vss (Vss=0 V)" is established. A response close to that of the step-type gas response SGR illustrated in FIG. 1 can be achieved (herein, there is no problem even in the flipping inversion).

In addition, from a different point of view, the catalytic gate CMOS inverter can be adjusted if each catalytic gate CMOS inverter is placed under a gas environment with an already-known gas concentration, the input potential Vin is gradually increased from the low potential Vss, and the input potential Vin caused when the CMOS inverter is inverted is defined as Vin(D).

In other words, when the sensor response intensity ΔVg corresponding to the threshold concentration at which the alarm or the warning for the desired gas is desirably issued is defined as a sensor response threshold intensity ΔVgth, the input setting gate potential Vin(D) is determined by the input potential Vin caused when the CMOS inverter is inverted at the threshold concentration at which the alarm or the warning of the desired gas is desirably issued. Since the threshold input potential Vtc is determined by the characteristics of the CMOS inverter caused without the gas irradiation, the sensor response threshold intensity ΔVgth can be determined from a relation "ΔVgth=Vtc−Vin(D)" when the CMOS gas sensor at the already-known gas concentration is adjusted.

When the CMOS gas sensor is actually installed, the input setting gate potential Vin (D) of the CMOS inverter may be determined by Expression (12) using the adjustment result.

$$Vin(D)=Vtc-\Delta Vgth \quad \text{Expression (12)}$$

At this time, as illustrated in FIG. 6, the output potential Vout with respect to the sensor response intensity ΔVg becomes a similar function form to that of the operation of the CMOS inverter (see FIG. 4 described above) with taking the input potential Vin as ΔVg.

In a practical CMOS inverter, the step response of the threshold input potential Vtc with respect to the input potential Vin cannot be achieved in a strict sense, and the response characteristics are inclined. However, the output potential Vout can be replaced by a center point satisfying "(Vdd−Vss)/2".

Furthermore, there are some of other design items. In order to achieve the step-type gas response SGR illustrated in FIG. 1 describe above, it is required to make (Vtp+Vdd−Vtn) small. In addition, it is also required to optimize the design parameters such as the input setting gate potential Vin(D), the high potential Vdd, the threshold voltage Vtp of the pMOS transistor, the threshold voltage Vtn of the nMOS transistor, and the characteristic coefficient $\beta_R$.

For example, it is required to set the threshold voltage Vtn of the nMOS transistor to a positive voltage, set the threshold voltage Vtp of the pMOS transistor to a negative voltage, satisfy a relation "Vin(D)<Vtc" as a condition that secures the CMOS inverter is not inverted, and satisfy a relation "Vtn<Vtp+Vdd" as a condition that the CMOS inverter is established. In addition, as described below, a relation "Vtc=Vdd/2 (Vss=0)" is satisfied in a case of "$\beta_R=1$" and "Vtp=−Vtn", and therefore, the change of the temperature characteristics can be suppressed to be the smallest in the inverter characteristics having the most preferable symmetry.

In addition, if a plurality of sensor response threshold intensities ΔVgth are set, the corresponding input setting gate potential Vin(D) can be set, and therefore, a gas sensor which issues multiple warnings can be manufactured. The multiple warnings can be also issued by preparing a plurality of the same sensor chips so as to correspond to the plurality of settings. In addition, the multiple warnings can be also issued by preparing a plurality of catalytic gate CMOS inverters inside the same chip.

Meanwhile, the sensing principle which is common with the gas sensor having the MOS structure based on the catalytic gate is not different but the measurement of the shift amount of the threshold voltage. Therefore, it is required to devise the step-type gas response with respect to a low gas concentration to seta small sensor response threshold intensity ΔVgth. For the variation between the chips in the sensor response intensity ΔVg, the adjustment described above may be firstly performed, and the input setting gate potential Vin(D) may be determined. However, when time-dependent change of the threshold voltage is large, the low gas concentration to set the small sensor response threshold intensity ΔVgth is greatly affected.

In transfer characteristics of FIG. 6, the detected gas concentration is uncertain (characteristic variation, reproduction variation of the characteristics, etc.) in correspondence with the variation of the sensor response threshold intensity ΔVgth. However, in the limitation to the gas sensor having the Pt—Ti—O gate structure, the influence of the sensor response threshold intensity ΔVgth is small since the gas response intensity is extremely large as illustrated in FIG. 1 described above.

In addition, the gas sensor for the gas having a possibility of the gas explosion has a standard for installation of the gas sensor, which issues an alarm (with red lamp+voice sound) at 25% or lower of the explosion lower limit concentration and issues a warning (with red lamp flickering) at about 1% of the explosion lower limit concentration, and therefore, it is only required in this range to bring the variation of the sensor response threshold intensity ΔVgth within a certain range. For example, under 1 atmosphere pressure, it is only required to exactly detect a reference value 1% so as to be 3% or lower, and therefore, the detection can be sufficiently handled since there is a margin of 0.169 V between a hydrogen concentration of 1% and a hydrogen concentration of 3% as following the Expression (2).

Next, the following is explanation about a gas sensor which can suppress the temperature compensation (drift or variation) of the threshold voltage unique to the MOS structure not depending on the detection gas.

As illustrated in FIG. 3 described above, the temperature characteristics of the threshold voltages Vtp and Vtn in the nMOS transistor and the pMOS transistor are in anti-phase. In other words, when the temperature is increased, the threshold voltage Vtp of the pMOS transistor is shifted in the positive direction, and the threshold voltage Vtn of the nMOS transistor is shifted in the negative direction as expressed by the Expressions (3), (4), and (5). Furthermore, when the operation temperatures of the nMOS transistor and the pMOS transistor are equally changed, a temperature coefficient Kn and a temperature coefficient Kp defined by the Expressions (3) and (4) have almost the same value as each other.

Therefore, in a relation of "$\beta_R=1$" and "Vtn0=−Vtp0" are designed from the Expression (10), the threshold input potential Vtc of the logical inversion characteristics does not depend on the temperature change, and therefore, stable (no drifting) inverter characteristics can be achieved. In addition, as illustrated in the Expression (10), the variations of the threshold voltages which are changed in the anti-phase can be cancelled, and therefore, the variation of the threshold input potential Vtc itself is suppressed, and the gas detection accuracy is improved. In particular, the detection accuracy at the low gas concentration to set the small sensor response threshold intensity ΔVgth can be remarkably improved.

Meanwhile, when the gas irradiation of the hydrogen or others or the temperature change occurs from the reference temperature, threshold voltage changes ΔVthN and ΔVthP of the nMOS transistor and the pMOS transistor having the same catalytic gate structure as each other are expressed as follows.

$$\Delta VthN = \Delta Vg(n) + \Delta Vth(n) \qquad \text{Expression (13)}$$

$$\Delta VthP = \Delta Vg(p) - \Delta Vth(p) \qquad \text{Expression (14)}$$

The sensor response intensity ΔVg satisfies a relation "ΔVg(n)=ΔVg(p)", and a relation "ΔVth(n)≅ΔVth(p)" is satisfied.

The variations of the threshold voltages caused by the temperature in the nMOS transistor and the pMOS transistor are in the anti-phase. Therefore, in order to remove an amount of the variations of the threshold voltages caused by the temperature, it is only required to obtain ½ of summation of a sensor response intensity ΔVg(n) of the nMOS transistor and a sensor response intensity ΔVg(p) of the pMOS transistor.

On the other hand, the sensor response intensity ΔVg(n) of the nMOS transistor and the sensor response intensity ΔVg(p) of the pMOS transistor are in the same-phase, and therefore, the amount of the variations caused by the temperature characteristics can be obtained as ½ of a difference between the sensor response intensity ΔVg(n) of the nMOS transistor and the sensor response intensity ΔVg(p) of the pMOS transistor. In this manner, the sensor response intensity ΔVg can be correctly obtained.

Figure 7:
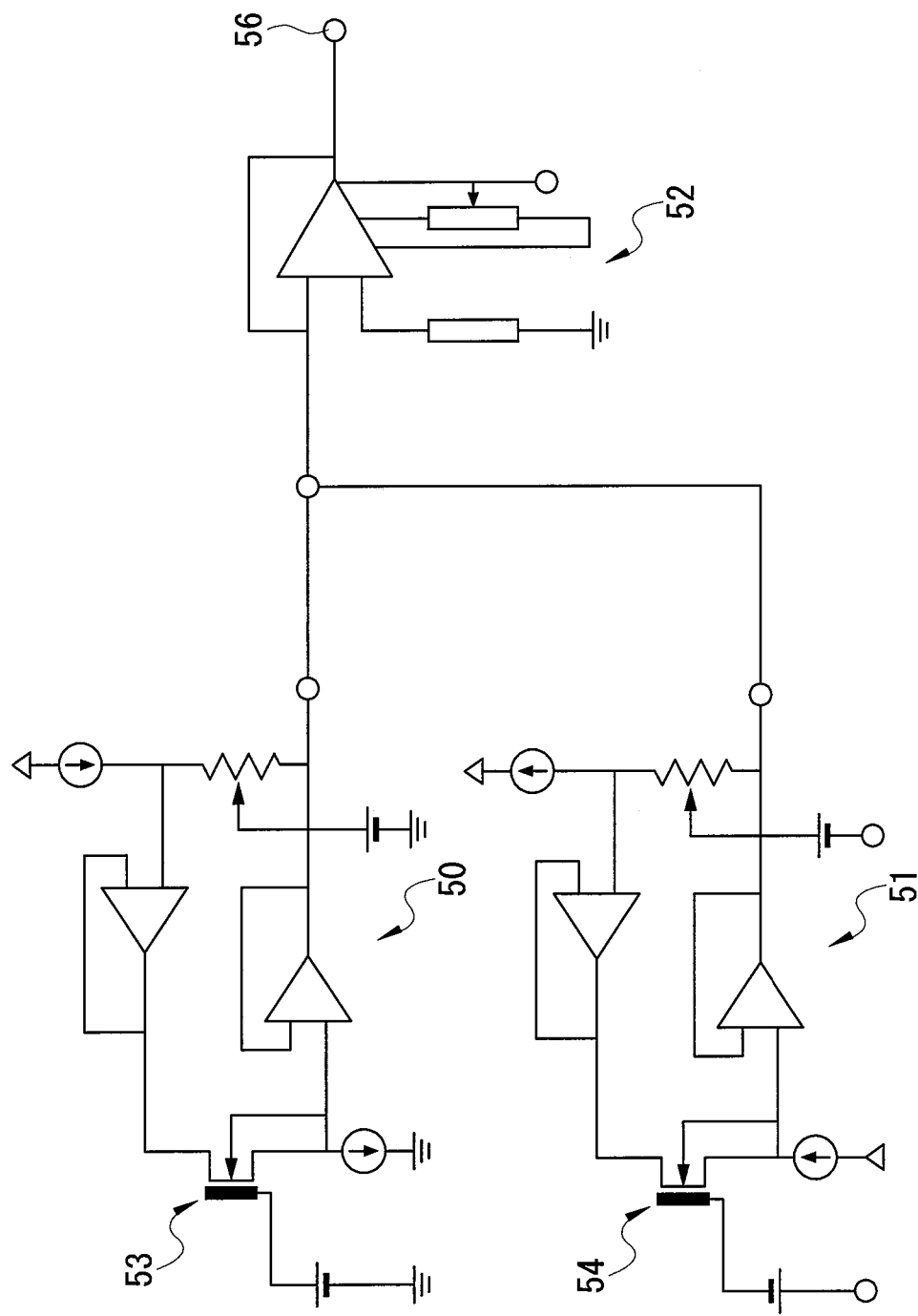
FIG. 7 is a schematic diagram describing an inverting summing amplifier circuit using an operational amplifier according to first and third embodiments.

The summation of the sensor response intensity ΔVg(n) of the nMOS transistor and the sensor response intensity ΔVg (p) of the pMOS transistor can be easily achieved by using an inverting summing amplifier circuit using an operational amplifier. FIG. 7 is a schematic diagram for describing the inverting summing amplifier circuit using the operational amplifier.

First, the voltage obtained by summation of the Expression (13) and the Expression (14) can be taken as the output signal of an output 56 of the inverting summing amplifier circuit by taking respective input voltage of an nMOS transistor 53 and a pMOS transistor 54 as the output voltage of inverting summing amplifier circuits 50 and 51 by using the voltage follower circuit, and summing the respective input voltages by an adder circuit 52. The subtraction of the output signal of the summed voltages by ½ is easy. If the gate structure of the nMOS transistor and the gate structure of the pMOS transistor are the same as each other, a relation "$\Delta Vg(n) \Delta Vg(p)$" is satisfied, and therefore, the signal (the sensor response intensity $\Delta Vg$) from which the temperature drift is removed can be taken out.

As described above, the signals which vary and drift in the anti-phase in the nMOS transistor and the pMOS transistor related to the threshold voltage can be removed by the above-described two methods if the magnitudes of both of the signals are equal to each other or so. For example, if the drift phenomenon occurs in the threshold voltage for a long time in the MOS gas sensor, the removal of the variation drift component by this method is effective.

Figure 8:
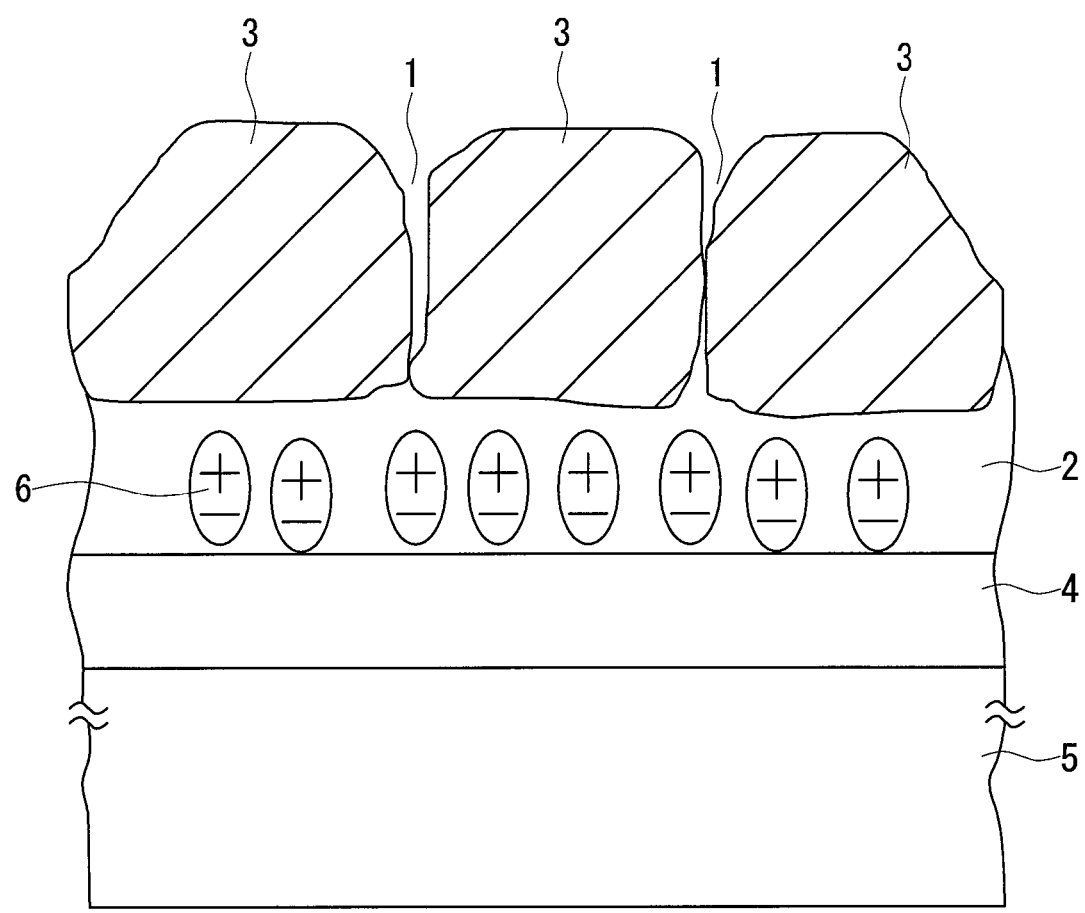
FIG. 8 is an enlarged cross-sectional view illustrating an enlarged gate structure of a catalytic gate CMOS-type hydrogen sensor according to the first embodiment.

Next, a gate structure of a catalytic gate CMOS-type hydrogen sensor according to the first embodiment will be described by using FIG. 8. FIG. 8 is an enlarged cross-sectional view illustrating the enlarged gate structure part of the catalytic gate CMOS-type hydrogen sensor. In the drawing, the hydrogen-atom induced dipole is denoted by the symbol 6.

A gate insulating film 4 (for example, a $SiO_2$ film) is formed on a Si substrate 5, and a Ti-modified film 2 is formed on the gate insulating film 4. Specifically, the Ti-modified film 2 is a film formed by mixing a TiO (titanium oxide) tiny crystal with an amorphous Ti film doped with oxygen. Its mixing ratio, thickness, and producing condition are described in, for example, Patent Documents 1, 2, and 3.

On the Ti-modified film 2, a film made of Pt crystal grains (also referred to as Pt grains or tiny crystals) 3 having (111) orientation is formed. A crystal boundary 1 is formed between the adjacent Pt crystal grains 3, and Ti, O, and Pt are formed in the grain-boundary vicinity region. While oxygen-doped Ti or TiO tiny particles are further formed on the surface of the grain-boundary vicinity region, these particles are not always necessary. The region formed by the Pt crystal grains 3 and the Ti-modified film 2 is called a Pt—Ti—O structure, and is used as the gate electrode of each of the nMOS transistor and the pMOS transistor. The Pt—Ti—O structure is manufactured by, for example, continuously stacking Ti and Pt on the gate insulating film 4, and then, being subjected to thermal treatment under oxygen atmosphere gas.

Next, the structure of the CMOS inverter of the catalytic gate CMOS-type hydrogen sensor according to the first embodiment will be described by using FIGS. 9 to 11. FIG. 9 is an example of a plan view of the CMOS inverter. FIG. 10 is a cross-sectional view of a principal part of the nMOS transistor configuring the CMOS inverter (a cross-sectional view of a principal part thereof taken along a line A-A' of FIG. 9). FIG. 11 is a cross-sectional view of a principal part of the pMOS transistor configuring the CMOS inverter (a cross-sectional view of a principal part taken along a line B-B' of FIG. 9).

A design example of the CMOS inverter will be described. In order to form the nMOS transistor and the pMOS transistor configuring the CMOS inverter so as to be symmetry, the gate electrode having the Pt—Ti—O structure and the gate insulating film are the same between the nMOS transistor and the pMOS transistor. If an effective mobility μn of the nMOS transistor is 250 $Cm^2/Vs$ and an effective mobility μp of the pMOS transistor is 75 $Cm^2/Vs$, it is possible to design the gate length Lg(n) of the nMOS transistor to be 20 μm, the gate width Wg(n) thereof to be 75 μm, the gate length Lg(p) of the pMOS transistor to be 20 μm, the gate width Wg(p) thereof to be 250 μm so that a relation "$\beta_R=\beta n/\beta p$" of the Expression (11) is 1.

The threshold voltage Vtn of the nMOS transistor is defined as a voltage obtained when the source-drain voltage Vds is 3.0 V and the source-drain current Ids is 10 μA, and is set to, for example, 1.3 V. Similarly, the threshold voltage Vtp of the pMOS transistor is defined as a voltage obtained when the source-drain voltage Vds is 3.0 V and the source-drain current Ids is 10 μA, and is set to, for example, -1.3 V.

Figure 9:
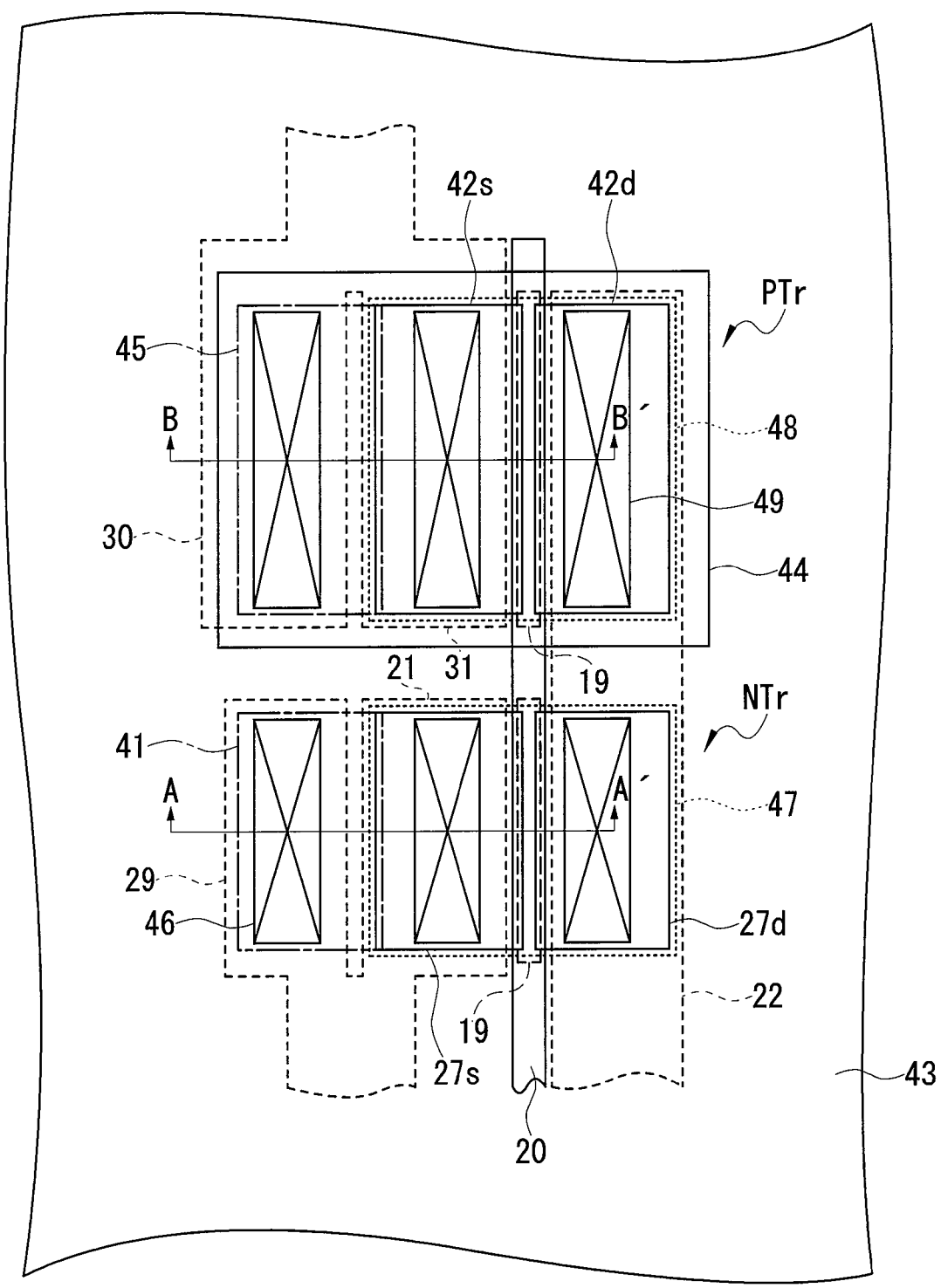
FIG. 9 is one example of a plan view of the CMOS inverter according to the first embodiment.
Figure 10:
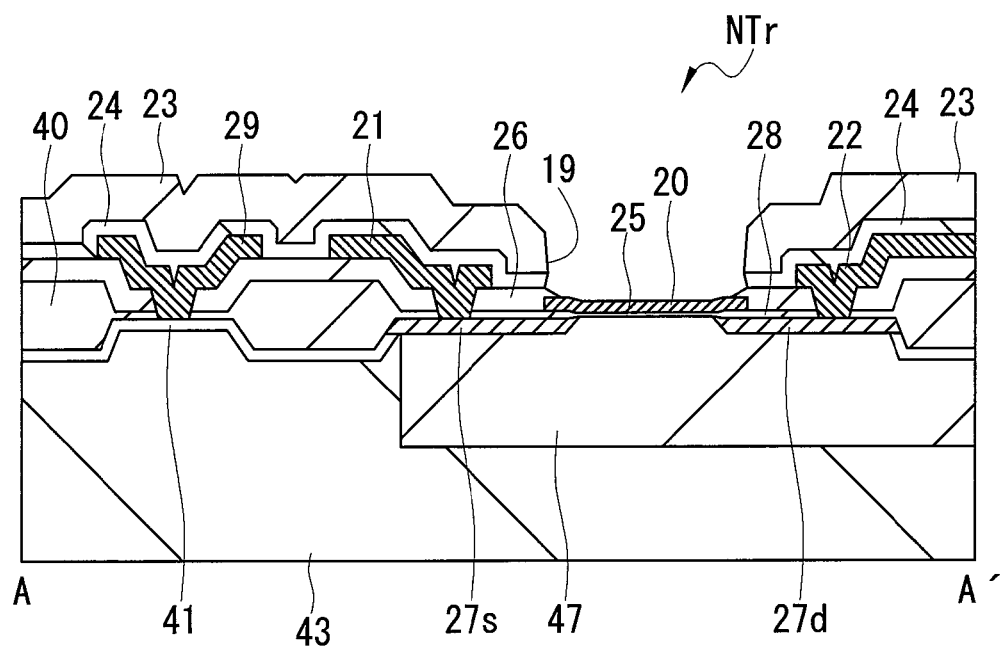
FIG. 10 is a cross-sectional view of a principal part of an nMOS transistor of the CMOS inverter according to the first embodiment (a cross-sectional view of a principal part thereof taken along a line A-A' of FIG. 9)
Figure 11:
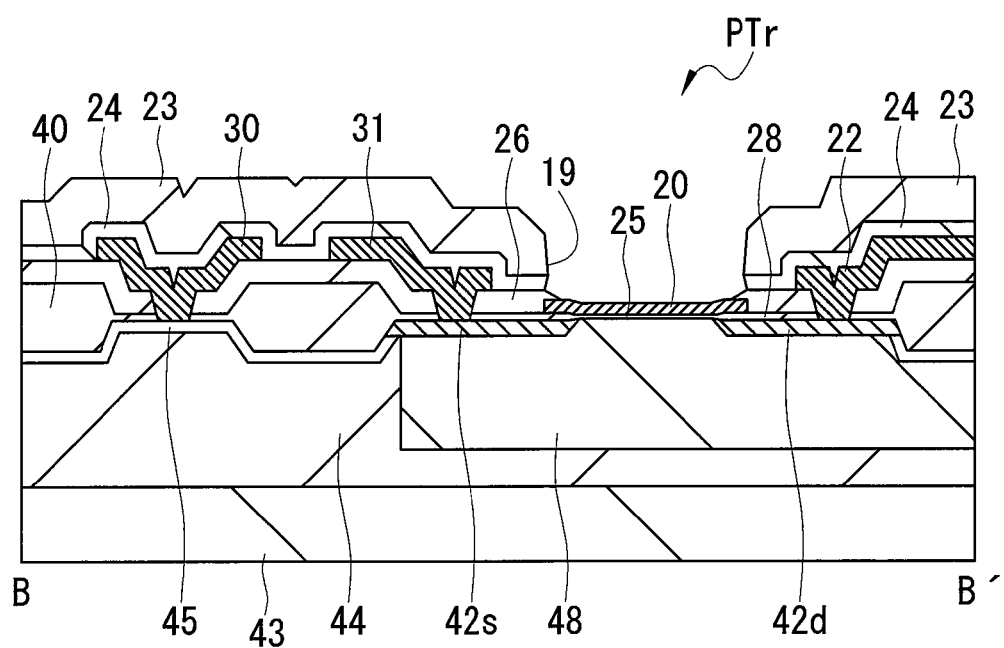
FIG. 11 is a cross-sectional view of a principal part of a pMOS transistor configuring the CMOS inverter according to the first embodiment (a cross-sectional view of a principal part thereof taken along a line B-B' of FIG. 9)

As illustrated in FIGS. 9 to 11, a control electrode 29 and a source electrode 21 which are connected to a p-type Si substrate 43 and a p-contact layer 41 of an nMOS transistor NTr are connected to each other, and are linked to the low potential terminal (a Vss terminal illustrated in FIG. 4 described above) of the CMOS inverter. In addition, a control electrode 30 and a source electrode 31 which are connected to an n-well 44 and an n-contact layer 45 of an pMOS transistor PTr are connected to each other, and are linked to the high potential terminal (a Vdd terminal illustrated in FIG. 4 described above) of the CMOS inverter. Because of the CMOS inverter, a drain region 27*d* of the nMOS transistor NTr and a drain region 42*d* of the pMOS transistor PTr are electrically connected to each other through a drain electrode 22, and are linked to the output terminal (Vout terminal illustrated in FIG. 4 described above) of the CMOS inverter.

On the other hand, a gate electrode 20 of the nMOS transistor NTr and a gate electrode 20 of the pMOS transistor PTr are connected to each other, and are linked to the input terminal (a Vout terminal illustrated in FIG. 4 described above) of the CMOS inverter. In this case, in the region which is exploded to the hydrogen gas, an opening 19 formed by removing a protection film made of a stacked film of a PSG (phosphosilicate glass) 24 and a silicon nitride film 23 is formed. The high potential (a Vdd illustrated in FIG. 4 described above) of the CMOS inverter is set to, for example, 3.0 V.

Next, a method of manufacturing the nMOS transistor NTr and the pMOS transistor PTr configuring the CMOS inverter will be described.

First, a method of manufacturing the nMOS transistor NTr will be described.

In the main surface of the p-type Si substrate 43, a film 40 of a local oxidation of silicon (LOCOS) is formed by local oxidation. The LOCOS-film 40 is configured by, for example, a $SiO_2$ film, and the thickness thereof is, for example, about 250 nm.

Next, in order to form an n-type channel region 47 in the main surface of the Si substrate 43, ion implantation of an n-type impurity (for example, phosphorous (P)) is performed with a dose amount of $8 \times 10^{11}/cm^2$. Thereafter, in order to form a source region 27*s* and a drain region 27*d*, ion implantation of an n-type impurity is performed, so that an active layer of the nMOS transistor NTr is formed.

Next, after performing a pre-treatment, agate insulating film 25 is formed in the main surface of the Si substrate 43 by a wet thermal oxidation method. The gate insulating film

25 is formed by, for example, a $SiO_2$ film, and the thickness thereof is, for example, about 18 nm. In addition, by the wet thermal oxidation method, a LOCOS-film 28 having a thickness of about 80 nm is formed in the surface of the n-type channel region 47 of the source region 27s and the drain region 27d.

Thereafter, the gate electrode 20 made of a Ti film (whose illustration is omitted) and a Pt film is formed on the gate insulating film 25 by, for example, a liftoff method. The thickness of the Ti film is, for example, about 5 nm, and the thickness of the Pt film is, for example, about 15 nm.

At this time, as illustrated in FIG. 9, the source region 27s and the drain region 27d are formed in accordance with the LOCOS-film 28 which defines a forming region of the gate electrode 20, and the gate electrode 20 is formed to cover not only an upper portion of the gate insulating film 25 but also an upper portion of a frame of the LOCOS-film 40 except. Therefore, the gate electrode 20 is formed so that the end of the gate electrode 20 is overlapped with the upper portion of the end of the source region 27s and the upper portion of the end of the drain region 27d. The Ti film and the Pt film configuring the gate electrode 20 are formed by, for example, an electron beam evaporation method.

Next, annealing at a thermal treatment temperature of 400° C. for a thermal treatment period of time of 2 hours is performed in the air atmosphere with high purity, so that the gate structure illustrated in FIG. 8 is formed.

Thereafter, an insulating film 26 which is made of the PSG (phosphosilicate glass) is formed on the Si substrate 43 including the upper portion of the gate electrode 20. Then, a contact hole passing through the insulating film 26 is formed, and subjected to a process such as surface treatment. Then, the source electrode 21, the drain electrode 22, and the control electrode 29, made of an Al (aluminum) film containing Si, are formed on the insulating film 26 including the inner side of the contact hole. Each thickness of the source electrode 21, the drain electrode 22, and the control electrode 29 is, for example, about 500 nm.

While illustration is omitted, as a heater for heating a lead line of the gate electrode 20 and the chip, a wiring made of an Al film containing Si as similar to the source electrode 21 or the drain electrode 22 is also formed. The width of the wiring heater is, for example, about 20 μm, and the wiring length is, for example, about 30,000 μm.

Next, in order to protect the source electrode 21, the drain electrode 22, the control electrode 29, and the chip, a protection film is formed on the main surface of the Si substrate 43. The protection film is configured by, for example, a stacked film of the PSG (phosphosilicate glass) 24 and the silicon nitride film 23. A silicon nitride film 24 is formed by a low temperature plasma CVD method, and the thickness of the protection film is, for example, about 700 nm.

Finally, a contact hole 46 is formed on an electrode pad (illustration is omitted) for the connection to a bonding wire, and the opening 19 is formed to expose the gate electrode 20 which is a sensor portion.

Next, a method of manufacturing the pMOS transistor PTr will be described. A method of manufacturing the pMOS transistor PTr is the same as that of the nMOS transistor NTr described above, and only a difference thereof will be described.

After the n-well 44 is formed in the p-type Si substrate 43, the local oxidation is performed, so that the LOCOS-film 40 is formed. The thickness of the LOCOS-film 40 is, for example, about 250 nm. Next, in order to forma p-type channel region 48 in the main surface of the Si substrate 43, ion implantation of a p-type impurity (for example, boron (B)) is performed with a dose amount of $3\times10^{12}/cm^2$. Thereafter, in order to form a source region 42s and a drain region 42d, ion implantation of the p-type impurity is performed, so that an active layer of the pMOS transistor PTr is formed.

Thereafter, as similar to the nMOS transistor NTr, the gate insulating film 25, the gate electrode 20, the source electrode 21, the drain electrode 22, and others are formed. Generally, at the time of the formation of the PSG (phosphosilicate glass), hydrogen annealing at 400° C. for 30 minutes under a 1% hydrogen gas is performed, and a hydrogen termination is performed.

In the catalytic gate CMOS-type hydrogen sensor, the temperature of the sensor chip is set to be equal to or higher than 100° C. for a response speed and desorption of moisture under environment.

In the first embodiment, if the threshold value is set to the 1% hydrogen concentration, the sensor response threshold intensity ΔVgth in accordance with the Expression (2) is 0.81 V. When it is assumed that the sensor response threshold intensity ΔVgth is set to 0.81 V, "Vdd=3.0 V" and "Vss=0.0 V" are satisfied, and thus "Vtc=1.5 V" is satisfied, and "Vin(D)=0.69 V" is satisfied by the Expression (12) as the input setting gate potential Vin(D).

Therefore, when the input setting gate potential Vin(D) is set to 0.69 V, the CMOS inverter in the catalytic gate CMOS-type hydrogen sensor is inverted under the hydrogen concentration which is 1% or higher, so that "Vout=0.0 V" is shown. Furthermore, under the hydrogen concentration which is lower than 1%, Vout returns to the initial value "Vout=3.0 V".

By this method, the desired threshold hydrogen concentration can be simply determined without using the analog circuit and the AD converter.

If a plurality of the threshold hydrogen concentrations are set, for example, the concentrations in the hydrogen leakage warning level of 500 ppm which is the low concentration, the system warning level of 0.5%, and others may be set for the sensor response threshold intensity ΔVgth as they are, and the input setting gate potential Vin(D) may be determined by the Expression (12) in consideration of the threshold input potential Vtc. This case has three types of the sensor response threshold intensities ΔVgth, and therefore, three catalytic gate CMOS-type hydrogen sensors are required. At that time, three sensor chips may be prepared or three catalytic gate CMOS-type hydrogen sensors may be formed in the same chip as one another, so that the desired input setting gate potentials Vin (D) can be set in each catalytic gate CMOS-type hydrogen sensor.

The first embodiment has described the example of the limitation of "$\beta_R=1$" and "Vtp=−Vtn" so that the temperature drift of the threshold voltage does not cause the variation of the threshold input potential Vtc. However, if the sensor response threshold intensity ΔVgth is large, influence of the variation of the threshold input potential Vtc is small, and therefore, it is not always required to set the above-described limitation.

Hereinafter, a method and a measure to solve the problems will be described.

(1) Regarding First Problem

The CMOS inverter having a catalytic gate electrode is introduced, and the input setting gate potential Vin(D) of the CMOS inverter is set to satisfy "ΔVgth=Vtc−Vin(D)". Herein, ΔVgth represents a sensor response threshold intensity corresponding to a desired gas concentration at which the alarm or the warning is desirably issued, and Vtc represents a threshold input voltage of the CMOS inverter. If there are a plurality of the desired threshold concentrations at which the alarm or the warning is desirably issued, a plurality of sensor response threshold intensities ΔVgth corresponding to the respective gas concentrations are prepared, and the input setting gate potential Vin(D) is designed to satisfy "ΔVgth=Vtc−Vin(D)" in each of the CMOS inverters.

(1) Regarding Second Problem

The CMOS inverter having a catalytic gate electrode is introduced, and the input setting gate potential Vin(D) of the CMOS inverter is set to satisfy "ΔVgth=Vtc−Vin(D)". Herein, ΔVgth represents a sensor response threshold intensity corresponding to a desired gas concentration at which the alarm or the warning is desirably issued, and Vtc represents a threshold input voltage of the CMOS inverter. And, the input setting gate potential Vin(D) is designed to be variable in accordance with the desired sensor response threshold intensity ΔVgth.

(3) Regarding Third Problem

The threshold input potential Vtc of the CMOS inverter is set so as to satisfy "$\beta_R=\beta n/\beta p=1$", and the threshold voltage Vtn0 of the nMOS transistor and the threshold voltage Vtp0 of the pMOS transistor are set so as to satisfy "Vtn0=−Vtp0" at a desired reference operation temperature. In addition, as described in the third embodiment below, in the nMOS transistor and the pMOS transistor having the same catalytic gate structure as each other, ½ of summation of the respective sensor response intensities is set to the sensor signal.

In the foregoing, in the explanation on the operation principle of the catalytic gate CMOS gas sensor, a case that the sensor response intensities ΔVg of the nMOS transistor and the pMOS transistor are the same as each other has been explained. However, even when the same catalytic gates are used, both of the sensor response intensities ΔVg are slightly different from each other in strict sense because of a manufacturing variation or others. Furthermore, if the catalytic gate structures of the nMOS transistor and the pMOS transistor are different from each other, the sensor response intensities ΔVg have different values from each other. If the sensor response intensities ΔVg of the nMOS transistor and the pMOS transistor are different from each other and the respective sensor response intensities are set to ΔVg(n) and ΔVg(p), the contents of the above description are changed in some points. Hereinafter, the points will be described.

If the catalytic gate CMOS gas sensor is exploded with a gas having a certain hydrogen concentration, the Expression (6) and the Expression (8) are modified as follows.

$$Ids=\beta n(Vin+\Delta Vg(n)-Vtn)^2/2 \qquad \text{Expression (15)}$$

$$Ids=\beta p(Vin+\Delta Vg(p)-Vdd-Vtp)^2/2 \qquad \text{Expression (16)}$$

When the source-drain currents Ids of the Expression (15) and the Expression (16) are set to be equal, the following Expression is obtained by using the threshold input potential Vtc of the logical inversion characteristics of the Expression (10).

$$\Delta Vgeff=Vtc-Vin \qquad \text{Expression (17)}$$

However, the ΔVgeff is an effective hydrogen response intensity of the catalytic gate CMOS gas sensor as defined by the following Expression.

$$\Delta Vgeff=[\sqrt{(\beta_R)}\Delta Vg(n)+\Delta Vg(p)]/(1+\sqrt{(\beta_R)}) \qquad \text{Expression (18)}$$

The ΔVgeff becomes an average value ΔVgav between the ΔVg(n) and the ΔVg(p) if "β=1" is satisfied.

$$\Delta Vgav=[\Delta Vg(n)+\Delta Vg(p)]/2 \qquad \text{Expression (19)}$$

A difference ΔVgdif between the ΔVg(n) and the ΔVg(p) is defined by the following Expression.

$$\Delta Vgdif=[\Delta Vg(n)-\Delta Vg(p)]/2 \qquad \text{Expression (20)}$$

The difference ΔVgdif can be also expressed by the following Expression using the average value ΔVgav and the difference ΔVgdif in general (also including a case of "$\beta_R \neq 1$").

$$\Delta Vgeff=\Delta Vgav+[\sqrt{(\beta_R)}-1]\Delta Vgdif/(1+\sqrt{(\beta_R)}) \qquad \text{Expression (21)}$$

It is considered that the nMOS transistor and the pMOS transistor have the sensor response intensity ΔVg(n) and the sensor response intensity ΔVg(p) different from each other when the nMOS transistor and the pMOS transistor are irradiated with the same hydrogen gas concentration. In this case, since a sensor response threshold intensity ΔVgth(n) of the nMOS transistor and a sensor response threshold intensity ΔVgth(p) of the pMOS transistor are different from each other, a new sensor response threshold intensity ΔVgeffth is defined as threshold intensity ΔVgth as follows by using the Expression (18).

$$\Delta Vgeffth=[\sqrt{(\beta_R)}\Delta Vgth(n)+\Delta Vgth(p)]/(1+\sqrt{(\beta_R)}) \qquad \text{Expression (22)}$$

In this case, the input setting gate potential Vin(D) of the CMOS inverter is obtained by using the following Expression instead of the Expression (12).

$$Vin(D)=Vtc-\Delta Vgeffth \qquad \text{Expression (23)}$$

In this manner, even if the sensor response intensities ΔVg of the nMOS transistor and the pMOS transistor are different from each other, the present invention can be achieved by replacing the sensor response threshold intensity ΔVgth with ΔVgeffth (Expression (22)). Therefore, the first embodiment has described only the case that the sensor response intensity ΔVg(n) of the nMOS transistor and the sensor response intensity ΔVg(p) of the pMOS transistor are the same as each other.

For example, when the value of the $\beta_R$ is near 1, the effective hydrogen response intensity ΔVgeff can be approximated to the average value ΔVgav between the sensor response intensity ΔVg(n) of the nMOS transistor and the sensor response intensity ΔVg(p) of the pMOS transistor, and the average value ΔVgav may be replaced with the sensor response intensity ΔVg described above.

Second Embodiment

In order to prevent drinking driving or check a hangover, a simple alcohol checker has been required, and a sensor which can exactly and simply check whether an alcohol is equal to or higher than a predetermined threshold concentration or not.

Difference points from the above-described first embodiment are that the catalytic gate structure is A configuration suitable for the alcohol gas, and that the sensor response threshold intensity ΔVgth is different since the catalytic gate structure is different and the sensor response intensity ΔVg in accordance with the alcohol gas concentration is different.

Accordingly, the second embodiment will describe an example of the catalytic gate structure which can determine an alcohol gas concentration of about 70 ppm in an air-diluted ethanol. An n-channel MOSFET gas sensor according to the second embodiment is disclosed in, for example, the above-described Patent Document 2.

The catalytic gate structure is different from that of the first embodiment since a gas concentration which is lower by 2 digits than that of the case of the explosion prevention of the hydrogen gas is a target, and it is also required to increase the sensor operation temperature. Since the circuit configuration is the same as the circuit configuration of the first embodiment, only a unique part to the alcohol sensor will be disclosed below.

Figure 12:
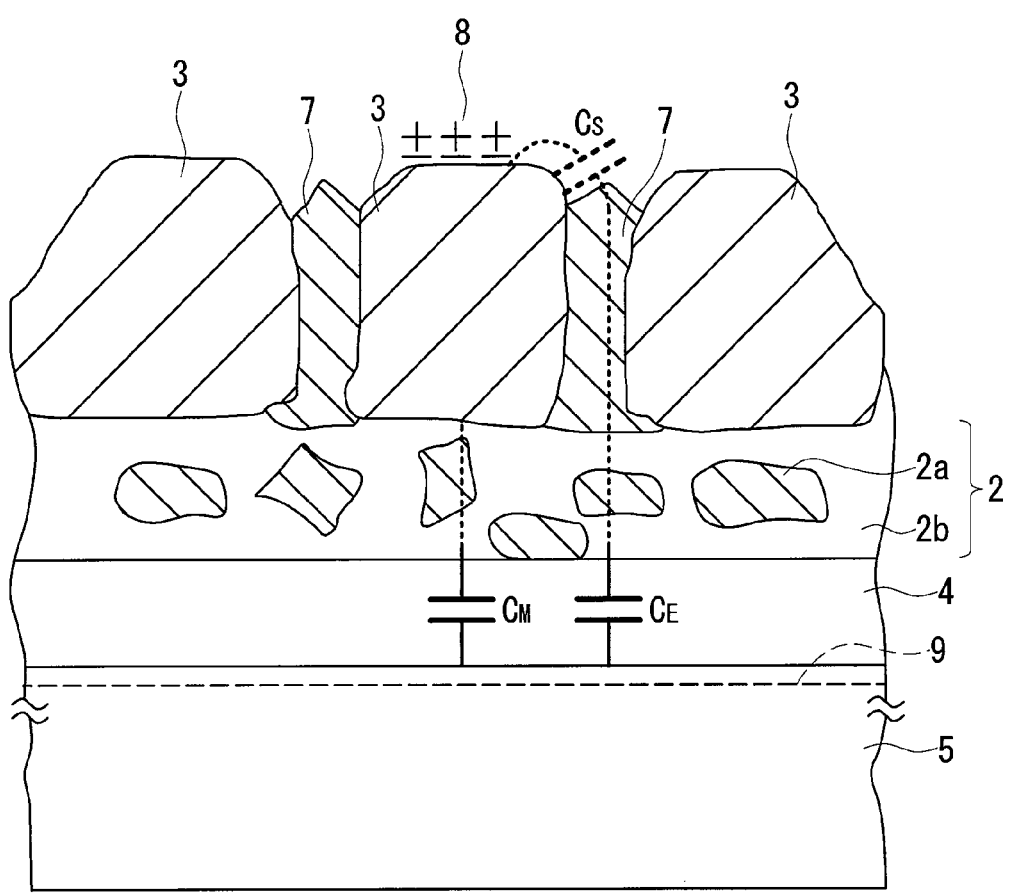
FIG. 12 is a schematic cross-sectional view illustrating an enlarged gate structure of a Si-MISFET gas sensor according to a second embodiment.

FIG. 12 is a schematic cross-sectional view illustrating the enlarged gate structure of a Si-MISFET gas sensor according to the second embodiment. The gate insulating film 4 (for example, a $SiO_2$ film) is formed on the Si substrate 5, and a mix film (herein, referred to as the Ti-modified film 2) of a TiOx nano-crystal 2a and an amorphous Ti film 2b doped with oxygen at a high concentration is formed on the gate insulating film 4. Furthermore, on the Ti-modified film 2, the (111)-oriented Pt crystal grains 3 which are effectively surrounded by a TiOx nano-structure 7 is formed. In addition, in FIG. 12, the polarization of the adsorbed polar molecules is denoted by the symbol 8, and a carrier inversion layer is denoted by the symbol 9.

The feature of this structure is different from the Pt—Ti—O gate structure illustrated in FIG. 8 described above in that an average gap between the adjacent Pt crystal grains 3 is wide, the Pt crystal grain 3 and the Pt crystal grain 3 are joined to each other by a capacitive coupling, and the electric short parts between the Pt crystal grain 3 and the Pt crystal grain 3 are less. In this manner, a molecule adsorption amount can be sensed by using a voltage change caused by the change in a surface voltage φs because of the adsorption gas expressed by the Expression (24) as a change amount ΔV of the threshold voltage (or a flat band voltage) of the MOS structure. Practically, an average distance between the adjacent Pt crystal grains 3 (an average inter-Pt grain boundary distance) is desirably set to about several nm in order to increase the electric capacity.

A large dielectric constant as that of the TiOx nano-structure 7, and a matter that carriers hardly exist in the TiOx nano-structure 7 are also the features. In this case, in the TiOx nano-structure 7, free carriers such as electrons or holes do not effectively exist, or exist little even if they exist.

A reason why the average distance between the adjacent Pt crystal grains 3 (the average inter-Pt grain boundary distance) is made to be small is to increase the electric capacity and to achieve the fully depletion in the TiOx nano-structure 7. Even in a conductive oxide having a carrier concentration of, for example, $10^{21}/cm^3$ or higher in a bulk state, the fully depletion of the TiOx nano-structure 7 can be achieved if the size is about several nm because of a Schottky barrier between the Pt crystal grain 3 and the TiOx nano-structure 7. However, the TiOx nano-structure 7 is in the fully depletion state at the operation temperature or is an insulator having no carrier.

When ethanol gas, ammonia gas, CO gas, or others are adsorbed on the surface of the Pt crystal grain 3, the effective molecular polarization is generated by an electric dipole due to asymmetry of the molecule itself or by the polarization of the molecule due to the adsorption even in the molecule having a high symmetry, so that the surface voltage φs of the Pt crystal grain 3 is changed. In this manner, regarding the capacitive system of an electric capacity $C_S$ between the Pt crystal grain 3 and the TiOx nano-structure 7 having no Pt on the surface of the gate insulating film 4, an electric capacity $C_E$ between a TOx nano-structure 7 and the carrier inversion layer 9, and an electric capacity $C_M$ between the Pt crystal grain 3 and the carrier inversion layer 9, the electric capacity $C_S$ and the electric capacity $C_E$ are connected in series, and the electric capacity $C_M$ is configured in parallel. Therefore, the change amount ΔV of the gate voltage has the following relation with respect to the change amount Δφs of the surface voltage φs, and the change amount ΔV of the gate voltage with respect to the gas adsorption can be observed.

$$\Delta V = \Delta \varphi s C_S \cdot C_E / [C_S \cdot C_E + C_M(C_S + C_E)] \quad \text{Expression (24)}$$

As described above, the gas sensor can detect the gas concentration as the change amount ΔVt of the gate voltage. In other words, the gas sensor can detect any gas as long as the gas changes the surface voltage φs of the Pt crystal grain 3 from the above-described operation principle. The change amount ΔV of the gate voltage may be regarded as the shift amount of the threshold voltage Vth, and can be applied to the catalytic gate CMOS gas sensor.

In the catalytic gate structure illustrated in FIG. 12, the Pt film and the Ti film formed by, for example, the electron beam evaporation method are heated at about 400° C. for about 2 hours in nitrogen atmosphere, and then, are more heated at about 400° C. for about 1 hour in the air. The thickness of the Pt film is, for example, about 7 nm, and the thickness of the Ti film is, for example, about 3 nm. Thereafter, the films are subjected to annealing process at the 1% hydrogen concentration.

Figure 13:
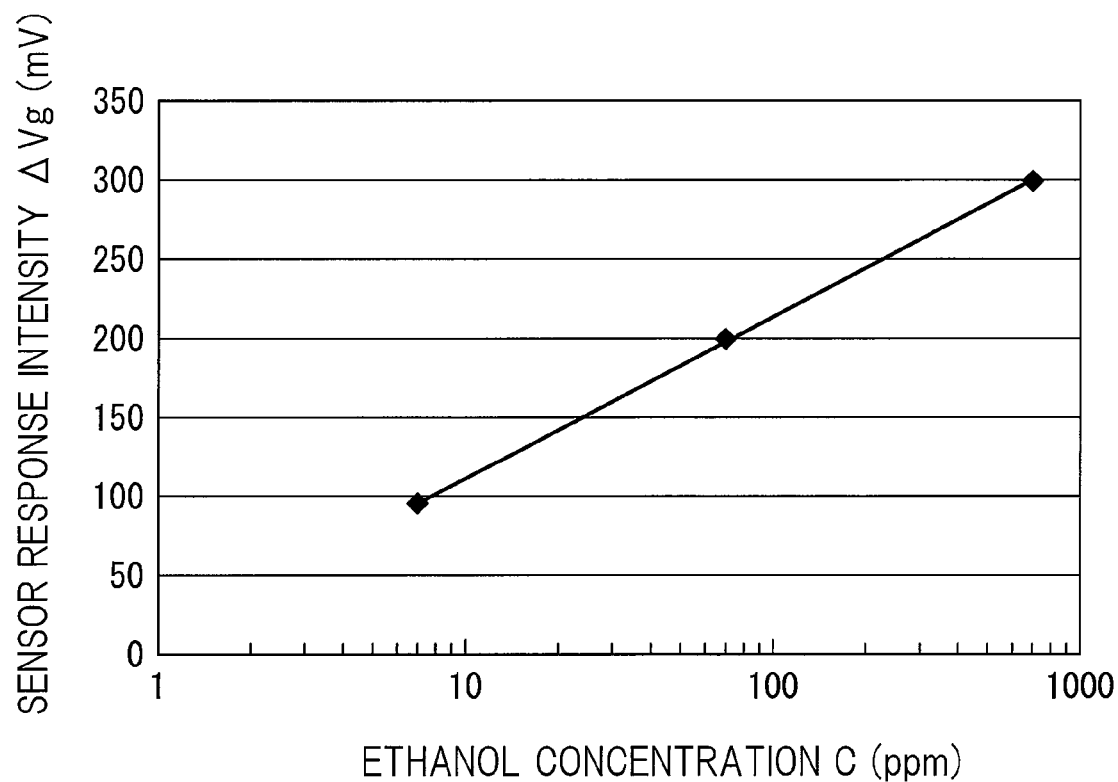
FIG. 13 is a graph illustrating an ethanol gas concentration dependency of the sensor response intensity (ΔVg) according to the second embodiment.

FIG. 13 is a graph illustrating an ethanol gas concentration dependency of the sensor response intensity (ΔVg). In the catalytic gate structure, when the sensor operation temperature is 180° C., a relation "ΔVgmax=400 mV" is satisfied in a relation "$C_0$=70 ppm" in a concentration range of 7 to 700 ppm, and it can be approximated by an Expression (25).

$$\Delta V(V) = \Delta V g \max[0.26 \text{ Log } C(\text{ppm})/C_0 + 0.5] \quad \text{Expression (25)}$$

In other words, when a desired threshold concentration is set to 70 ppm, a relation "ΔVgth=200 mV" is satisfied. In the catalytic gate structure illustrated in FIG. 12 described above, the CMOS inverter having the same planar dimension as that of the first embodiment is configured, a relation "Vtc=1.5 V" is set from relations "Vdd=3.0 V" and "Vss=0.0 V", and the input setting gate voltage Vin(D) is set so that a relation "Vin(D)=1.3 V" is satisfied from the Expression (12). In this case, the above-described catalytic gate CMOS inverter illustrated in FIG. 2 is inverted at an ethanol gas concentration of 70 ppm or higher, and thus, a relation "Vout=0.0 V" is shown. Furthermore, when the concentration is lower than the ethanol gas concentration of 70 ppm, the Vout returns to the initial value "Vout=3.0 V".

By this method, a desired threshold ethanol gas concentration can be simply determined without using the analog circuit and the AD converter, and a simply alcohol checker can be provided.

In the second embodiment, the sensor response threshold intensity ΔVgth is 200 mV which is lower than the sensor response threshold intensity ΔVgth of the first embodiment, and therefore, the reduction on the temperature drift is effective for the improvement of the measurement accuracy. If relations "$\beta_R$=1" and "Vtn0=−Vtp0" are designed from the Expression (10), the threshold input potential Vtc of the logical inversion characteristics can achieve the inverter characteristics which are stable (not drifted) regardless of the temperature change.

The catalytic gate structure of the second embodiment and the catalytic gate structure of the first embodiment are different from each other in the gate electrode, and accordingly the threshold voltage Vtn of the nMOS transistor and the threshold voltage Vtp of the pMOS transistor are unmatched with each other. In this case, a relation "Vtn=−Vtp=1.3 V" can be achieved by adjusting the ion implantation condition, particularly the dose, used when the channel region of the first embodiment is formed.

Third Embodiment

By forming the nMOS transistor and the pMOS transistor having the same catalytic gate structure as each other as similar to the first embodiment, the above-described circuit configuration illustrated in FIG. 7 can be achieved. This manner can remove a factor causing a variation in the anti-phase due to the variation of the threshold voltage of the sensor of the nMOS transistor and the pMOS transistor.

In the first embodiment, the wiring is performed for the CMOS inverter (both gates of the nMOS transistor and the pMOS transistor are the catalytic gate). However, in the third embodiment, the nMOS transistor and the pMOS transistor are formed independently to each other, the sensor response intensity $\Delta Vg$ of each of them is extracted as the output of the above-described voltage follower circuit illustrated in FIG. 7, and is added to the input of the inversion adder circuit, so that the gas sensor is achieved.

Figure 14:
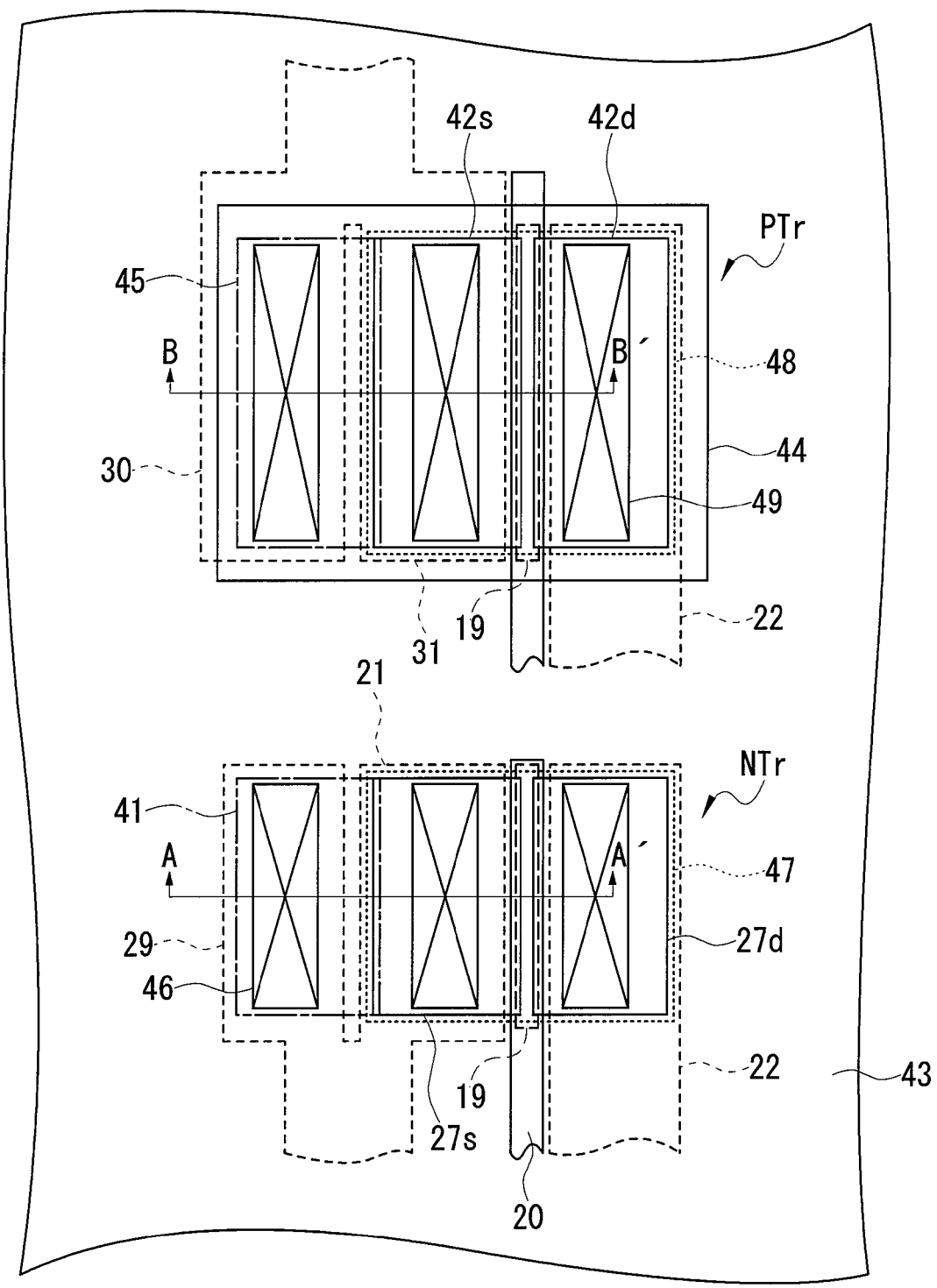
FIG. 14 is one example of a plan view of a pMOS transistor and an nMOS transistor configuring a gas sensor according to a third embodiment.

FIG. 14 illustrates an example of a plan view of the pMOS transistor and the nMOS transistor configuring the gas sensor.

The gate length and the gate width of each of the pMOS transistor PTr and the nMOS transistor NTr are the same as those of the CMOS inverter described in the first embodiment. However, the case of the above-described inverting adder amplifier circuit illustrated in FIG. 7 is effective in the nMOS transistor NTr and the pMOS transistor PTr to remove the signal component varying and drifting in the anti-phase even without the limitations of "$\beta_R=1$" and "Vtp=−Vtn" related to the CMOS inverter, and the design rule can be moderated, and therefore, the gas sensor can be simply manufactured.

Fourth Embodiment

In above-described first, second and third embodiments, the Si semiconductor is used. A fourth embodiment will explain a catalytic gate CMOS gas sensor which uses a SiC semiconductor and which can be used in a high temperature environment of about 300 to 700° C.

Figure 15:
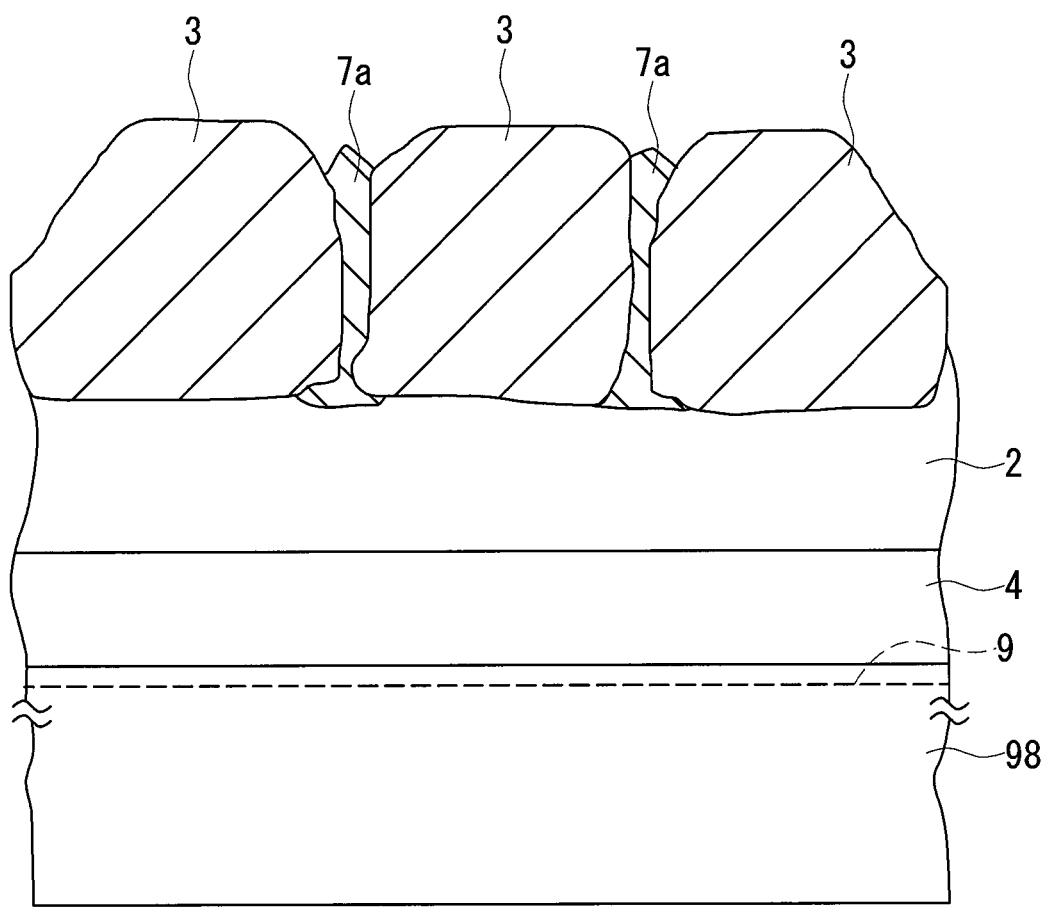
FIG. 15 is a schematic cross-sectional view illustrating an enlarged gate structure of a catalytic gate CMOS-type hydrogen sensor according to a fourth embodiment.

FIG. 15 is a schematic cross-sectional view illustrating an enlarged gate structure of a catalytic gate CMOS-type hydrogen sensor according to the fourth embodiment. The catalytic gate has an improved Pt—Ti—O gate structure in which a ratio of the TiOx crystal portion in the modified Ti film is larger than that of the oxygen-doped amorphous Ti portion.

The Pt film is configured by a plurality of Pt crystal grains 3, O and Ti exist in a crystal boundary space 7a between the plurality of Pt crystal grains 3, and more particularly, the TiOx nano-crystal is formed (as a modified Pt film) centrally a surface in vicinity of grain-boundary triple points. FIG. 15 illustrates an example in which a boundary between a SiC channel layer 98 and the gate insulating film 4 has the carrier inversion layer 9 depending on the gate voltage.

In the improved Pt—Ti—O gate structure, for example, a Ti film is formed on the gate insulating film (a $SiO_2$ film) 4, and a Pt film is further formed on the Ti film. The thickness of the Ti film is, for example, about 5 nm, and the thickness of the Pt film is, for example, about 15 nm. Thereafter, the annealing is performed in the air at 400° C. for 68 days. Alternatively, the annealing may be performed in the air at 600° C. for about 12 hours.

The fact that the improved Pt—Ti—O/$SiO_2$/SiC substrate structure employing the Pt—Ti—O gate structure is stable is different from a Pt/$SiO_2$/SiC substrate structure in which Pt is directly formed on the gate insulating film 4. The improved Pt—Ti—O/$SiO_2$/SiC substrate structure is suitable for the application of the operation for a long time at 400 to 600° C.

In the fourth embodiment, the circuit configuration of the catalytic gate CMOS inverter is the same as that of the first embodiment. However, the performance thereof is different from that of the catalytic gate CMOS-type hydrogen sensor of the first embodiment.

Next, the catalytic gate CMOS-type hydrogen sensor having the improved Pt—Ti—O gate structure according to the fourth embodiment will be described by using FIGS. 16 to 18. FIG. 16 is an example of a plan view illustrating an example of the CMOS inverter. FIG. 17 is a cross-sectional view of a principal part of the nMOS transistor configuring the CMOS inverter (a cross-sectional view of a principal part taken along a line A-A' of FIG. 16). FIG. 18 is a cross-sectional view of a principal part of the pMOS transistor configuring the CMOS inverter (a cross-sectional view of a principal part taken along a line B-B' of FIG. 16).

First, a method of manufacturing the nMOS transistor NTr configuring the CMOS inverter will be described.

As illustrated in FIGS. 16 and 17, an n-type 4H—SiC8° off semiconductor substrate ($2 \times 10^{18}/cm^3$) is prepared. An n-type semiconductor layer 83 having a thickness of, for example, about 10 μm is formed on the semiconductor substrate by a homoepitaxial growth technique. The electron concentration of the n-type semiconductor layer 83 is, for example, $1 \times 10^{17}/cm^3$. Subsequently, in order to form a p well 84 in the n-type semiconductor layer 83, ions of a p-type impurity such as Al (aluminum) are implanted with a dose energy of, for example, 250 kV. B (boron) may be used for the p-type impurity.

Next, a LOCOS-film 90 is formed in the main surface of the n-type semiconductor layer 83 by the local oxidation. The LOCOS-film 90 is formed by, for example, a $SiO_2$ film, and the thickness thereof is, for example, about 250 nm.

Next, while an oxide film for defining the N channel region is used as a mask, ions of an n-type impurity such as N (nitrogen) are implanted into the p well 84, so that an n-type semiconductor layer (Vth adjusting n-ion implantation layer) 87 is formed. Furthermore, a source region 77s and a drain region 77d are formed so as to have an impurity concentration of the n-type impurity such as N (nitrogen) of $1 \times 10^{20}/cm^3$ and have a depth of about 200 nm from the surface of the n-type semiconductor layer 87. P (phosphorus) may be used for the n-type impurity.

Next, a p contact layer 81 is formed in order to control a substrate potential of the p well 84. Specifically, ions of Al (aluminum) are implanted into the p well 84. The dose energy is, for example, 70 keV, and the dose is, for example, $5 \times 10^{14}/cm^2$. After the ion implantation, the Ar annealing is performed at 1300° C. for 20 minutes in the Ar (argon) atmosphere. The annealing process may be individually performed after each ion implantation. In addition, a flash annealing method for 1 to 5 minutes may be used for the annealing process.

Next, after the pretreatment is performed on the n-type semiconductor layer 83, a gate insulating film 75 is formed by a wet oxidation method. The gate insulating film 75 is configured by, for example, a $SiO_2$ film, and the thickness thereof is, for example, about 30 nm. In the wet oxidation method, for example, a thermal oxidation at 850° C. for 30 minutes and a thermal oxidation at 1100° C. for 6 hours are performed. By the wet oxidation method, a LOCOS-film 78 having a thickness of about 80 nm is formed even in the surface of the n-type semiconductor layer 87 of the source region 77s and the drain region 77d. In the source region 77s and the drain region 77d, the vicinity of the surface of the n-type semiconductor layer 87 is formed in an amorphous state by the previous ion implantation, and therefore, oxidation is advanced, so that the LOCOS-film 78 thicker than the gate insulating film 75 is formed.

Next, in the Ar atmosphere (Ar-diluted 1% hydrogen) obtained by diluting the hydrogen concentration to 1%, the hydrogen annealing is performed at a thermal treatment temperature of 800 to 1000° C. for thermal treatment time of 30 minutes. In this case, improvement of a retaining force of a hydrogen terminal by using deuterium instead of hydrogen is the same as that of the first embodiment. For example, the hydrogen gas having a hydrogen concentration of 0.1 to 3.5% is used.

Thereafter, for example, by the liftoff method, a gate electrode 70 which is made by a Ti film (whose illustration is omitted) and a Pt film is formed on the gate insulating film 75. The Ti film and the Pt film are formed continuously. The thickness of the Ti film is, for example, about 5 nm, and the thickness of the Pt film is, for example, about 15 nm. In many cases, the thickness of the Ti film is selected in a range of, for example, 2 to 10 nm, and the thickness of the Pt film is selected in a range of, for example, 5 to 90 nm. If a high concentration hydrogen (for example, 20 to 70%) is detected, the thickness of the Pt film is increased to be, for example, about 90 nm. This is because, while the sensitivity in a low concentration region disappears due to the increase in the thickness thereof, the sensitivity in a high concentration region appears.

At this time, as illustrated in FIG. 17, the source region 77s and the drain region 77d are formed in accordance with the LOCOS-film 78 which defines a forming region of a gate electrode 75, and the gate electrode 70 is formed so as to cover not only an upper portion of the gate insulating film 75 but also an upper portion of an edge of the LOCOS-film 78. Therefore, the gate electrode 75 is formed so that the ends of the gate electrode 70 are overlapped with the upper portion of the end of the source region 77s and the upper portion of the end of the drain region 77d. This is because, in the fourth embodiment, a technique of forming the source region 77s and the drain region 77d so as to be self-alignment is not employed for the gate electrode 70. The Ti film and the Pt film are formed by, for example, the electron beam evaporation, at a film deposition rate of, for example, about 10 nm/min.

Next, the catalytic gate structure can be achieved by performing the annealing at a thermal treatment temperature of 400° C. for thermal treatment time of 68 days in the air of high purity, or the annealing at 600° C. for about 12 hours in the air thereof. Thereafter, in a nitrogen atmosphere having the concentration of hydrogen or deuterium of about 0.1 to 3.5%, the hydrogen annealing may be performed at a thermal treatment temperature of about 400 to 630° C. for thermal treatment time of 30 minutes.

Next, an insulating film 76 made of PSG (phosphosilicate glass) or TEOS is formed on the n-type semiconductor layer 83 including the upper portion of the gate electrode 70. Then, a contact hole passing through the insulating film 76 is formed, and subjected to a process such as surface treatment.

Next, a source electrode 71, a drain electrode 72, and a control electrode 79 are formed by depositing a Ti film, a TiN film, and a Pt film are sequentially deposited on the n-type semiconductor layer 83 by an EB (physical vapor) deposition liftoff method, and processing them. The thickness of the Ti film is, for example, about 50 nm, the thickness of the TiN film is, for example, about 50 nm, and the thickness of the Pt film is, for example, about 300 nm.

Next, the source electrode 71, the drain electrode 72, the control electrode 79, and a protection film for protecting the chip are formed on the main surface of the n-type semiconductor layer 83. The protection film is configured by, for example, a stack film of a PSG (phosphosilicate glass) 74 and a silicon nitride film 73.

Finally, a contact hole 86 is formed on an electrode pad (whose illustration is omitted) for the connection to a bonding wire, and an opening 99 is formed so as to expose the gate electrode 70 which is a sensor portion therefrom.

Next, a method of manufacturing the pMOS transistor PTr configuring the CMOS inverter will be described. Note that the same part as the above-described method of manufacturing the nMOS transistor NTr will be omitted.

As illustrated in FIGS. 16 and 18, while an oxide film for defining the P channel region is used as a mask, ions of a p-type impurity such as Al (aluminum) is implanted into the n-type semiconductor layer 83, so that a p-type semiconductor layer (Vth adjusting p-ion implantation layer) 88 is formed. Furthermore, a source region 82s and a drain region 82d are formed so as to have the impurity concentration of the p-type impurity such as Al (aluminum) of $1 \times 10^{20}/cm^3$ and a depth of about 200 nm from the surface of the p-type semiconductor layer 88.

Next, an n contact layer 85 is formed in order to control the substrate potential of the n-type semiconductor layer 83. Specifically, ions of N (nitrogen) are implanted into the n-type semiconductor layer 83. The dose energy is, for example, 20 keV, and the dose is, for example, $5 \times 10^{14}/cm^2$. Thereafter, the annealing process is performed as similar to the nMOS transistor NTr.

Next, as similar to the nMOS transistor NTr, the gate insulating film 75, the gate electrode 70, and others are formed, and then, the insulating film 76 made of PSG (phosphosilicate glass) or TEOS is formed on the n-type semiconductor layer 83 including the upper portion of the gate electrode 70. Then, a contact hole passing through the insulating film 76 is formed, and subjected to a process such as surface treatment. Furthermore, as similar to the nMOS transistor NTr, a source electrode 91, the drain electrode 72, and a control electrode 80 are formed on the n-type semiconductor layer 83.

The lead lines of the gate electrodes 70 of the nMOS transistor NTr and the pMOS transistor PTr are omitted. In addition, although illustration is omitted, as a heater for heating the chip, the wiring heater may be formed by using the stacked film formed by the Ti film, the TiN film, and the Pt film configuring the source electrodes 71 and 91 and others. A wiring width of the wiring heater is, for example, about 20 μm, and a wiring length thereof is, for example, about 29,000 μm.

In order to symmetrically arrange the nMOS transistor and the pMOS transistor configuring the CMOS inverter, the gate electrode having the Pt—Ti—O structure and the gate insulating film are the same as each other between the nMOS transistor and the pMOS transistor. If an effective mobility μn of the nMOS transistor is 50 $Cm^2/Vs$ and an effective mobility μp of the pMOS transistor is 20 $Cm^2/Vs$, it can be so designed that the gate length Lg(n) of the nMOS transistor and the gate length Lg(p) of the pMOS transistor both are set to 10 μm so as to be the same as each other, the gate width Wg(n) of the nMOS transistor is set to 200 μm, and the gate width Wg(p) of the pMOS transistor is set to 500 μm so that a relation "$\beta_R=\beta n/\beta p$" of the Expression (11) becomes 1.

The threshold voltage Vtn of the nMOS transistor is defined as a voltage when the source-drain voltage Vds is 3.0 V and the source-drain current Ids is 10 μA, and is set to, for example, 1.3 V. Similarly, the threshold voltage Vtp of the pMOS transistor is defined as a voltage when the source-drain voltage Vds is −3.0 V and the source-drain current Ids is 10 μA, and is set to, for example, −1.3 V. The other circuit configurations are the same as those of the first embodiment, and thus, the description for them will be omitted.

In the fourth embodiment, as the concentration dependency on the hydrogen gas, a relation "$\Delta gmax=2.0$ V" is satisfied in a relation "$C_0=1\%$" in a concentration range of 0.1 to 10% when the sensor operation temperature is 500° C., and can be approximated by the Expression (25).

In other words, a relation "$\Delta Vgth=1.0$ V" is satisfied by setting a desired threshold concentration to 1%, and therefore, the CMOS inverter having the same planar dimension as that of the first embodiment is configured, a relation "Vtc=1.5 V" is set from relations "Vdd=3.0 V" and "Vss=0.0 V", and the input setting gate potential Vin(D) is set so as to satisfy a relation "Vin(D)=0.5 V" from the Expression (12). In this case, the above-described catalytic gate CMOS inverter illustrated in FIG. 2 is inverted at a hydrogen gas concentration of 1% or higher, and thus a relation "Vout=0.0 V" is shown. Furthermore, when the hydrogen gas concentration is lower than 1%, the Vout returns to the initial value "Vout=3.0 V".

By this method, a desired threshold hydrogen gas concentration can be simply determined without using the analog circuit and the AD converter, so that the hydrogen concentration threshold value at a high temperature can be simply measured.

The catalytic gate structure of the fourth embodiment and the catalytic gate structure of the first embodiment are different from each other in the gate electrode, and accordingly the threshold voltage Vtn of the nMOS transistor and the threshold voltage Vthp of the pMOS transistor are unmatched with each other. This case can achieve to satisfy a relation "Vtn=−Vtp=1.3 V" by adjusting the ion implantation condition, more particularly, the dose used when the channel region of the first embodiment is formed.

In the foregoing, the invention made by the present inventor has been concretely described based on the embodiments. However, it is needless to say that the present invention is not limited to the foregoing embodiments and various modifications and alterations can be made within the scope of the present invention.

The gas sensor may be configured by using a field effect transistor having a structure other than the MOS structure described in first to fourth embodiments. For example, a TFT (Thin Film Transistor) formed on a glass substrate may be used. The TFT has been applied mainly to an image element. However, since the nMOS transistor and the pMOS transistor can be manufactured on the same substrate, it is needless to say that the gas sensor can be achieved by applying a suitable catalytic gate structure to a desired gas. In other words, the nMOS transistor and the pMOS transistor in which the catalytic gate structure is formed so as to be applicable to the CMOS inverter may be achieved.

In addition, in the first to fourth embodiments, the nMOS transistor and the pMOS transistor are formed on the same chip as each other, both gates are arranged to be close to each other as much as possible in order to avoid the influence of the variation in process. However, the invention is not limited to this. For example, the nMOS transistor and the pMOS transistor may be manufactured on different chips from each other.

SIGN LIST 1 crystal boundary
2 Ti modified film
2a TiOx nano crystal
2b amorphous Ti film
3 Pt crystal grain
4 gate insulating film
5 silicon substrate
6 hydrogen atom induced dipole
7 TiOx nano structure
7a crystal boundary space
8 polarization of adsorbed polar molecules
9 carrier inverting layer
19 opening
20 gate electrode
21 source electrode
22 drain electrode
23 silicon nitride film
PSG (phosphosilicate glass)
25 gate insulating film
26 insulating film
27d drain region
27s source region
28 LOCOS film
29, 30 control electrode
31 source region
40 LOCOS film
41 p-contact layer
42d drain region
42s source region
43 silicon substrate
44 n-well
45 n-contact layer
46 contact hole
47 n-channel region
48 p-channel region
49 contact hole
50, 51 inverting summing amplifier circuit
52 adder circuit unit
53 n-MOS transistor
54 p-MOS transistor
56 output
70 gate electrode
source electrode
72 drain electrode
73 PSG (phosphosilicate glass)
silicon nitride film
75 gate insulating film
76 insulating film
77d drain region
77s source region
78 LOCOS film
79, 80 control electrode
81 p-contact layer
82d drain region
82s source region
83 semiconductor layer
84 p-well
85 n-contact layer
86 contact hole
87 semiconductor layer
88 semiconductor layer 89 contact hole
90 LOCOS film
98 SiC channel layer
99 opening
NTr n-MOS transistor
PTr p-MOS transistor
SGR step-type gas response

The invention claimed is:

1. A semiconductor gas sensor comprising:
an n-channel field effect transistor that includes a first gate having catalysis; and
a p-channel field effect transistor that includes a second gate having catalysis,
wherein a concentration of gas is detected by using a first sensor response intensity indicating a shift amount of a threshold voltage of the n-channel field effect transistor and a second sensor response intensity indicating a shift amount of a threshold voltage of the p-channel field effect transistor, and
wherein a gate width of the p-channel field effect transistor is greater than a gate width of the n-channel field effect transistor such that a characteristic coefficient of the n-channel field effect transistor ($\beta n$) and a characteristic coefficient of the p-channel field effect transistor ($\beta p$), based on an effective mobility of the p-channel field effect transistor and an effective mobility of the n-channel field effect transistor, satisfy the relationship $\beta_R = \beta n / \beta p = 1$ so that the first gate of the n-channel field effect transistor and the second gate of the p-channel field effect transistor have a same symmetrical configuration with respect to each other.

2. The semiconductor gas sensor according to claim 1, wherein the gas is hydrogen gas, hydrogen compound gas, or polar molecule gas.

3. The semiconductor gas sensor according to claim 1, wherein ½ of summation of the first sensor response intensity of the n-channel field effect transistor and the second sensor response intensity of the p-channel field effect transistor is set as a sensor signal.

4. The semiconductor gas sensor according to claim 1, wherein the n-channel field effect transistor and the p-channel field effect transistor configure a CMOS inverter.

5. The semiconductor gas sensor according to claim 4, wherein the first gate of the n-channel field effect transistor and the second gate of the p-channel field effect transistor are not covered by a protection film.

6. The semiconductor gas sensor according to claim 4, wherein, if a threshold input potential of the CMOS inverter is expressed as "Vtc" and the first sensor response intensity of the n-channel field effect transistor and the second sensor response intensity of the p-channel field effect transistor generated by a concentration of a gas to be detected are expressed as "$\Delta Vgth(n)$" and "$\Delta Vgth(p)$", respectively, the following relations are satisfied, $Vtn = -Vtp > 0$, and an input setting gate potential Vin(D) of the CMOS inverter is set as follows by using $\Delta Vgeffth$ defined as "$\Delta Vgeffth = [\sqrt{(\beta_R)} \Delta Vgth(n) + \Delta Vgth(p)] / (1 + \sqrt{(\beta_R)})$":

$Vin(D) = Vtc - \Delta Vgeffth$, where Vtn is the threshold voltage of the nMOS transistor and Vtp is the threshold voltage of the pMOS transistor.

7. The semiconductor gas sensor according to claim 4, wherein, if a threshold input potential of the CMOS inverter is expressed as "Vtc", and each of the first sensor response intensity of the n-channel field effect transistor and the second sensor response intensity of the p-channel field effect transistor generated by a concentration of a gas to be detected is expressed as "$\Delta Vgth$",
an input setting gate potential Vin(D) of the CMOS inverter is set as follows:

$Vin(D) = Vtc - \Delta Vgth$.

8. The semiconductor gas sensor according to claim 4, wherein, if a threshold input potential of the CMOS inverter is expressed as "Vtc", each of the first sensor response intensity of the n-channel field effect transistor and the second sensor response intensity of the p-channel field effect transistor generated by a first gas concentration to be detected is expressed as "$\Delta Vgth1$", and each of the first sensor response intensity of the n-channel field effect transistor and the second sensor response intensity of the p-channel field effect transistor generated by a second gas concentration to be detected, which is different from the first gas concentration, is expressed as "$\Delta Vgth2$",
when the first gas concentration is detected,
a first input setting gate potential Vin(D)1 of the CMOS inverter is set as follows, $Vin(D)1 = Vtc - \Delta Vgth1$, and, when the second gas concentration is detected,
a second input setting gate potential Vin(D)2 of the CMOS inverter is set as follows:

$Vin(D)2 = Vtc - \Delta Vgth2$.

9. The semiconductor gas sensor according to claim 4, wherein, if each of the first sensor response intensity of the n-channel field effect transistor and the second sensor response intensity of the p-channel field effect transistor generated by concentrations of gases to be detected is expressed as "$\Delta Vgth(N)$" in accordance with N conditions,
when an I-th gas concentration having the threshold input potential of the CMOS inverter expressed as "Vtc(I)" and having the first sensor response intensity and the second sensor response intensity expressed as "$\Delta Vgth(I)$" is detected,
the I-th input setting gate potential Vin(D)I of the CMOS inverter is set as follows, $Vin(D)I = Vtc(I) - \Delta Vgth(I)$, and the semiconductor gas sensor is configured by N CMOS inverters,
where N is the number of conditions and I is one of a plurality of gas concentrations.

10. The semiconductor gas sensor according to claim 9, wherein the N CMOS inverters are configured on the same substrate as one another.

11. The semiconductor gas sensor according to claim 4, wherein, when a potential of the CMOS inverter on a low potential side is expressed as "Vss", a potential of the CMOS inverter on a high potential side is expressed as "Vdd", a threshold potential of the n-channel field effect transistor is expressed as "Vtn", a threshold potential of the p-channel field effect transistor is expressed as "Vtp", and a threshold input potential of the CMOS inverter is expressed as "Vtc", the following relations are satisfied:

$Vtn>0,$ $Vtp<0,$ and $Vdd+Vtp>Vtc>Vtn.$

12. The semiconductor gas sensor according to claim 4, wherein, when a threshold potential of the n-channel field effect transistor is expressed as "Vtn", a threshold potential of the p-channel field effect transistor is expressed as "Vtp", a threshold input potential of the CMOS inverter is expressed as "Vtc",
the following relation is satisfied:

$Vtn=-Vtp>0.$

13. The semiconductor gas sensor according to claim 4, wherein a heater region is arranged so as to be adjacent to a region where the n-channel field effect transistor and the p-channel field effect transistor are arranged.

14. The semiconductor gas sensor according to claim 1, wherein the n-channel field effect transistor and the p-channel field effect transistor are formed in different regions from each other in a main surface of a semiconductor substrate,
the n-channel field effect transistor includes:
  (a) a first gate insulating film that is formed on the semiconductor substrate;
  (b) a first gate electrode that is formed on the first gate insulating film;
  (c) a first source region that is formed in the semiconductor substrate; and
  (d) a first drain region that is formed in the semiconductor substrate,
the p-channel field effect transistor includes:
  (e) a second gate insulating film that is formed on the semiconductor substrate;
  (f) a second gate electrode that is formed on the second gate insulating film;
  (g) a second source region that is formed in the semiconductor substrate; and
  (h) a second drain region that is formed in the semiconductor substrate, and
the first gate electrode of the n-channel field effect transistor and the second gate electrode of the p-channel field effect transistor are configured by
  (i) a titan-modified film that is formed by mixing an oxygen-doped titanium film containing oxygen with a titanium tiny crystal, and
  (j) a platinum film that is formed on the titan-modified film.

15. The semiconductor gas sensor according to claim 14, wherein the platinum film is configured by a plurality of crystal grains, and oxygen and titan exist in a grain boundary region among the plurality of crystal grains.

16. The semiconductor gas sensor according to claim 14, wherein the first drain region of the n-channel field effect transistor and the second drain region of the p-channel field effect transistor are electrically connected to each other, and
the first gate electrode of the n-channel field effect transistor and the second gate electrode of the p-channel field effect transistor are electrically connected to each other.

17. The semiconductor gas sensor according to claim 1, wherein a heater region is arranged so as to be adjacent to a region where the n-channel field effect transistor and the p-channel field effect transistor are arranged.

18. The semiconductor gas sensor according to claim 1, wherein
the gate width of the p-channel field effect transistor is 250 μm,
the gate width of the n-channel field effect transistor is 75 μm, and
a gate length of the p-channel field effect transistor and the n-channel field effect transistor is the same.

* * * * *